United States Patent
Imai et al.

(10) Patent No.: US 10,517,619 B2
(45) Date of Patent: Dec. 31, 2019

(54) MEDICAL DEVICE AND METHOD FOR TREATMENT

(71) Applicant: TERUMO KABUSHIKI KAISHA, Shibuya-ku, Tokyo (JP)

(72) Inventors: Masaomi Imai, Kanagawa (JP); Yuuki Masubuchi, Kanagawa (JP); Takashi Kitaoka, Kanagawa (JP); Takahiro Chida, Kanagawa (JP); Kazuaki Kanamoto, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 282 days.

(21) Appl. No.: 15/439,364

(22) Filed: Feb. 22, 2017

(65) Prior Publication Data
US 2017/0238949 A1 Aug. 24, 2017

(30) Foreign Application Priority Data
Feb. 23, 2016 (JP) .................. 2016-031781

(51) Int. Cl.
*A61B 17/22* (2006.01)
*A61B 17/3207* (2006.01)
*A61B 17/00* (2006.01)
*A61B 17/32* (2006.01)

(52) U.S. Cl.
CPC ...... *A61B 17/22* (2013.01); *A61B 17/320758* (2013.01); *A61B 2017/00867* (2013.01); *A61B 2017/22001* (2013.01); *A61B 2017/22002* (2013.01); *A61B 2017/22079* (2013.01); *A61B 2017/22084* (2013.01); *A61B 2017/320052* (2013.01)

(58) Field of Classification Search
CPC .......... A61B 17/221; A61B 17/320725; A61B 17/320758; A61B 2017/320716; A61B 2017/00867; A61B 2017/22001; A61B 2017/22002; A61B 2017/22038; A61B 2017/22067; A61B 2017/2212; A61F 2002/016; A61F 2/013; A61F 2002/011; A61F 2230/0069; A61F 2/01
USPC ........................................................ 606/200
See application file for complete search history.

(56) References Cited

U.S. PATENT DOCUMENTS 5,800,520 A * 9/1998 Fogarty .................... A61F 2/07
606/194
8,562,637 B2 10/2013 Kusleika
(Continued)

*Primary Examiner* — Katherine M Shi
(74) *Attorney, Agent, or Firm* — Buchanan Ingersoll & Rooney PC

(57) ABSTRACT

A medical device designed to be inserted into a lumen of a living body so as to block a flow of fluid in the lumen of the living body. The medical device includes: a long shaft part; an expandable part; and a covering part. The expandable part is an elastically deformable cylindrical body, and the cylindrical body having a proximal part connected to the shaft part. The covering part takes on a cylindrical shape and is flexible and deformable independently of the expandable part, and the cylindrical shape has a proximal part connected to a proximal part of the expandable part or connected to the shaft part located at a proximal side with respect to the expandable part. The covering part defines a space in the radial direction between a distal side end part of the cylindrical shape and the expandable part.

19 Claims, 20 Drawing Sheets

(56) References Cited

U.S. PATENT DOCUMENTS

| | | | |
|---|---|---|---|
| 2009/0198269 A1* | 8/2009 | Hannes | A61B 17/221 606/200 |
| 2013/0317589 A1* | 11/2013 | Martin | A61F 2/06 623/1.2 |
| 2014/0005712 A1* | 1/2014 | Martin | A61B 17/221 606/200 |

* cited by examiner

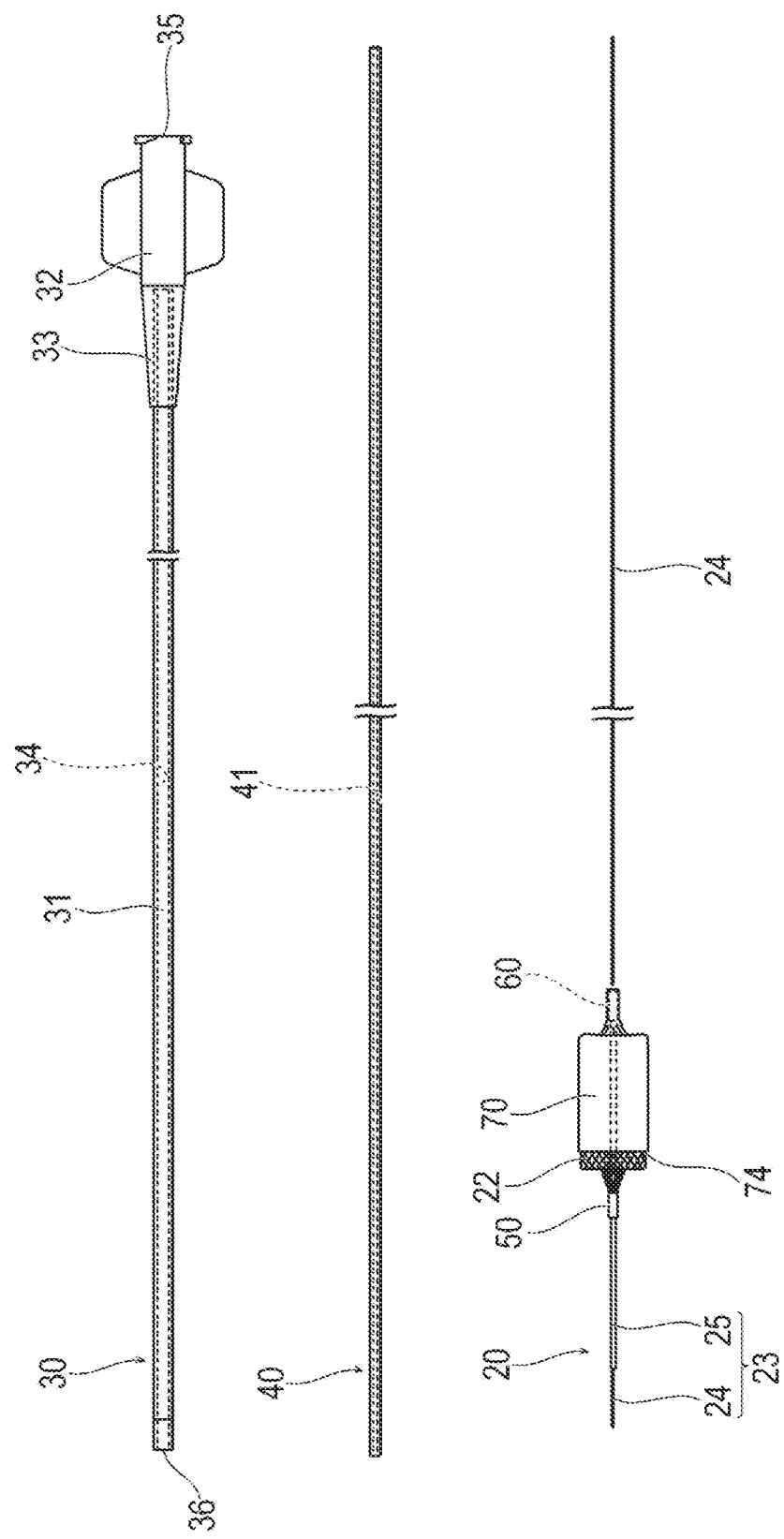

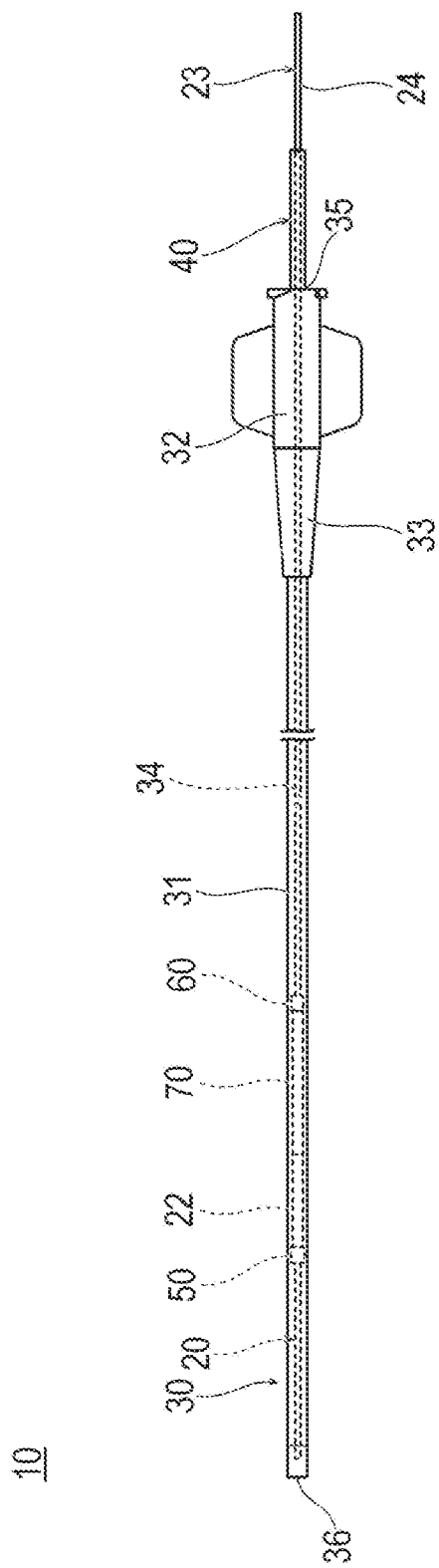

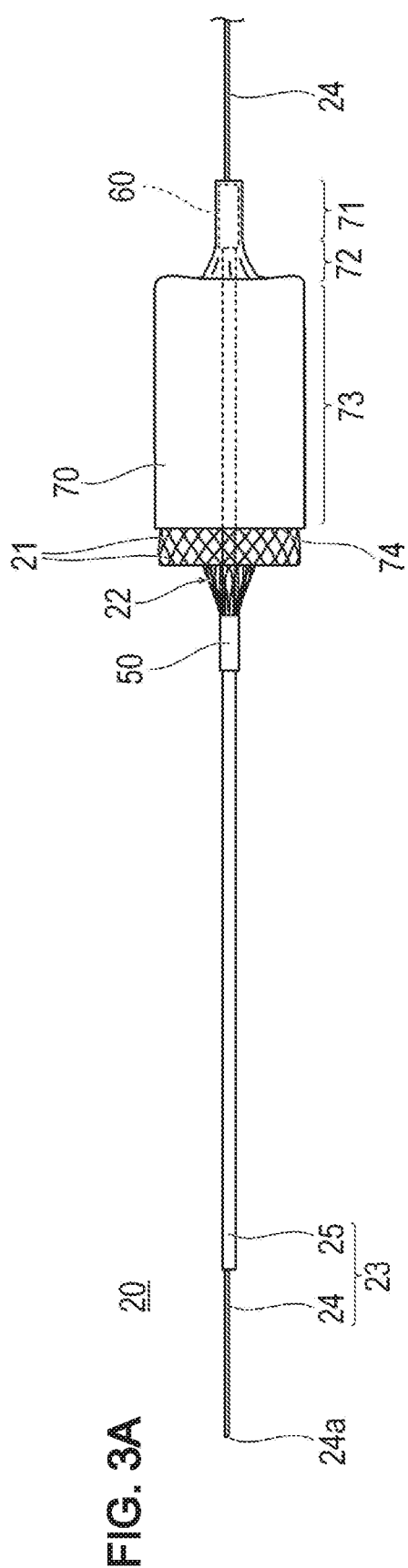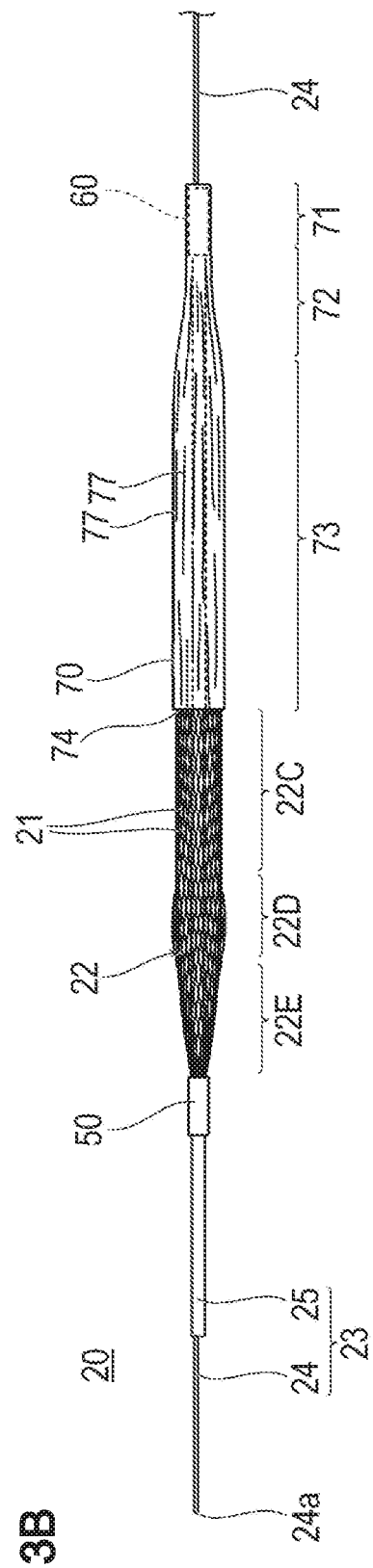

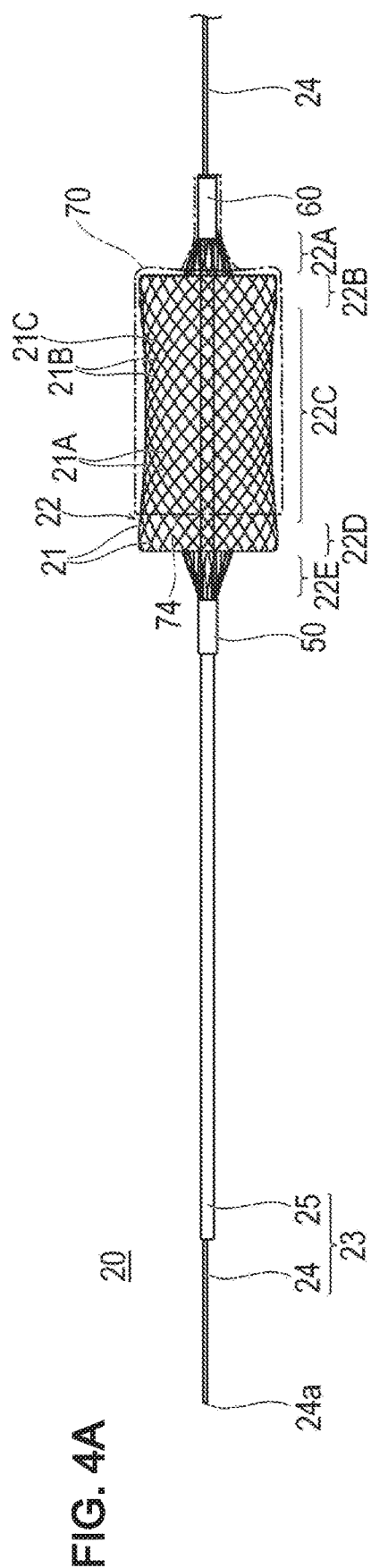
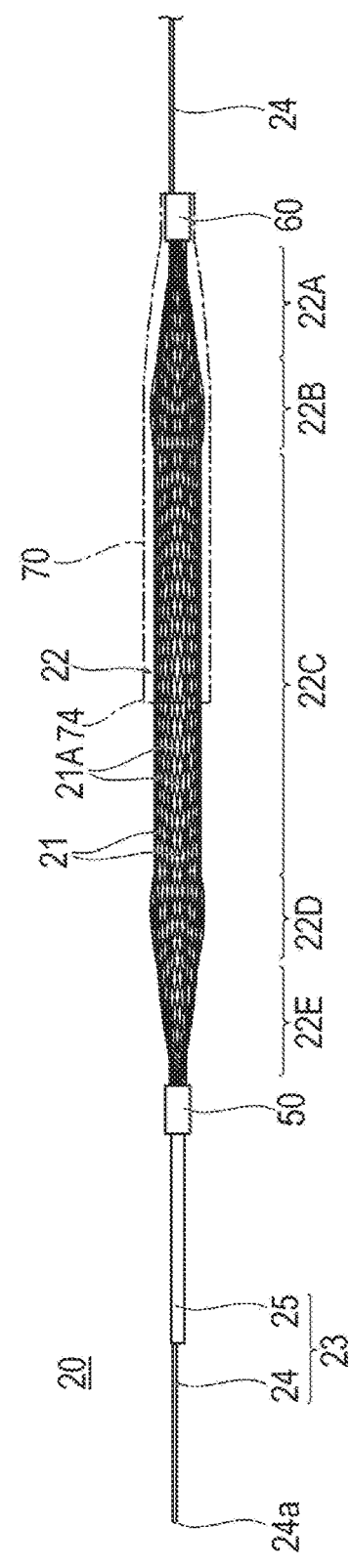
FIG. 4A
FIG. 4B

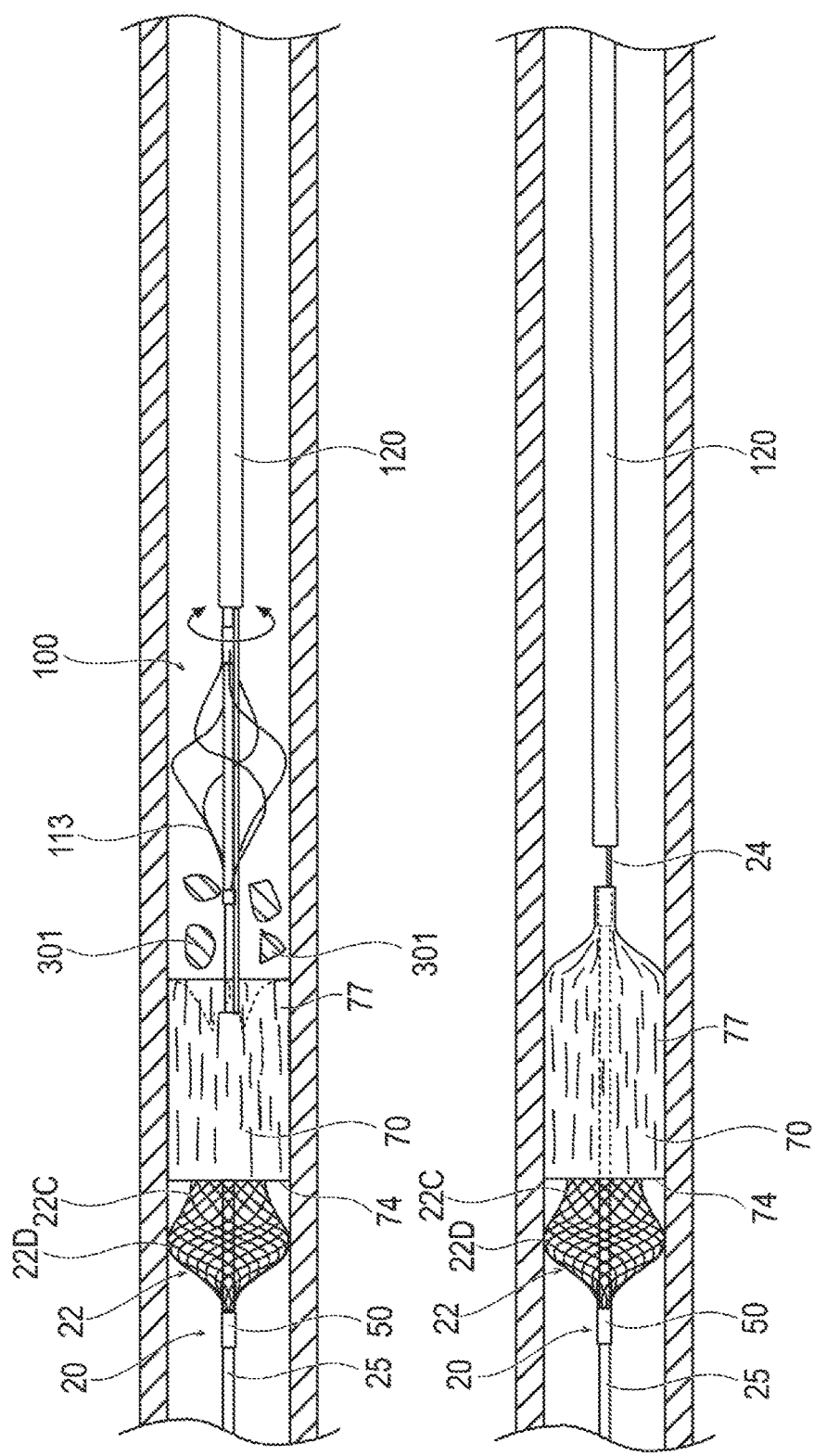

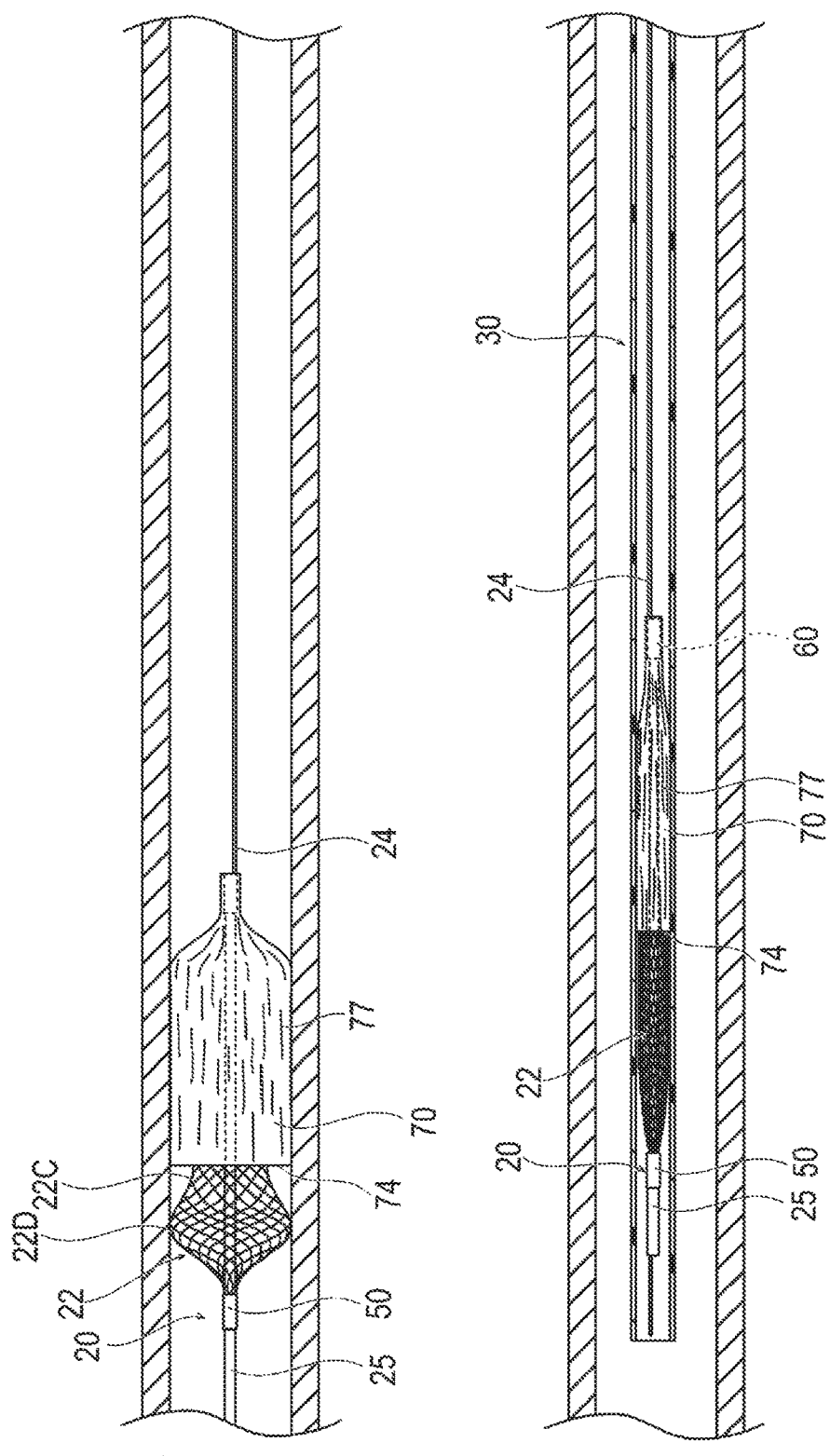

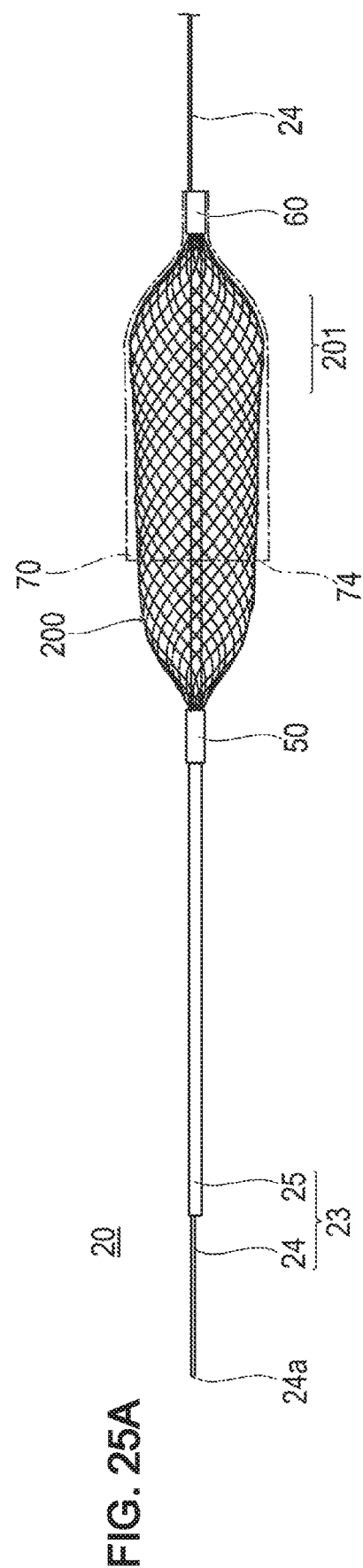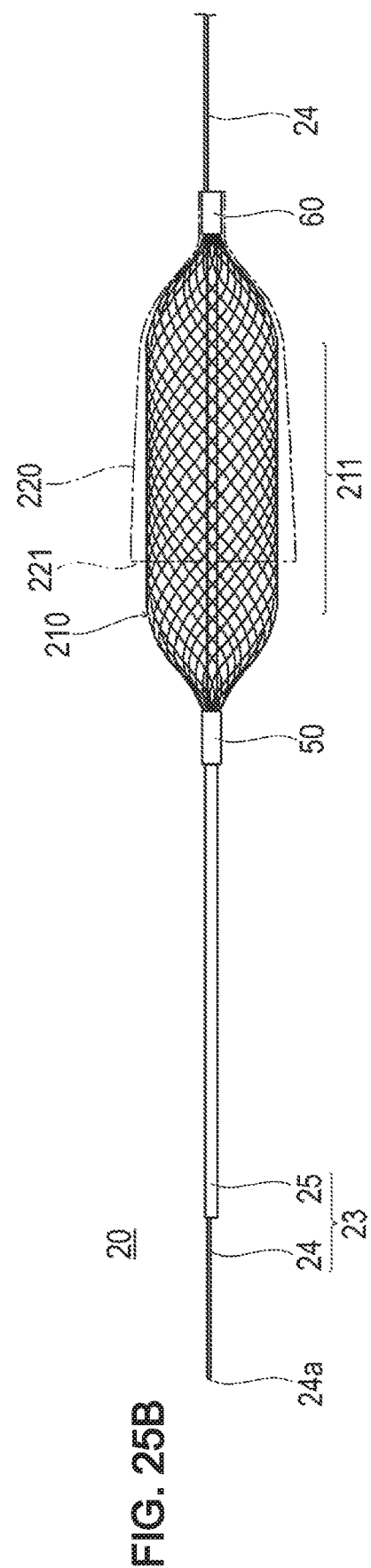

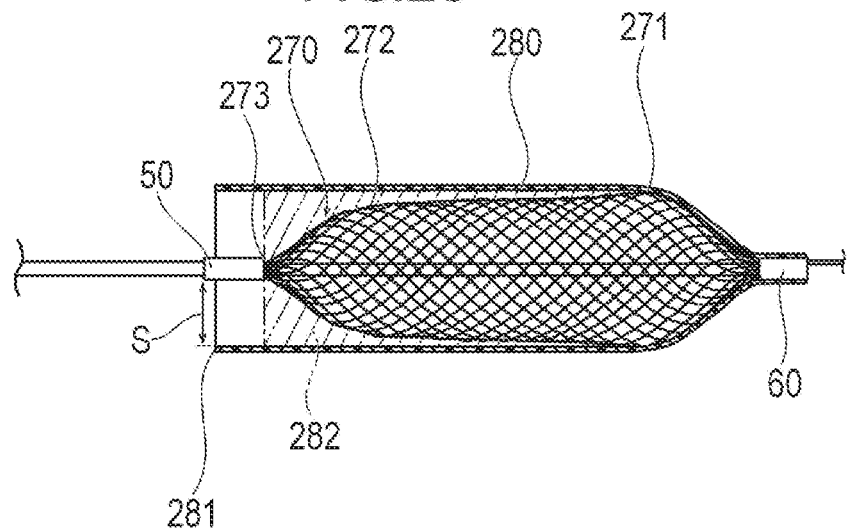
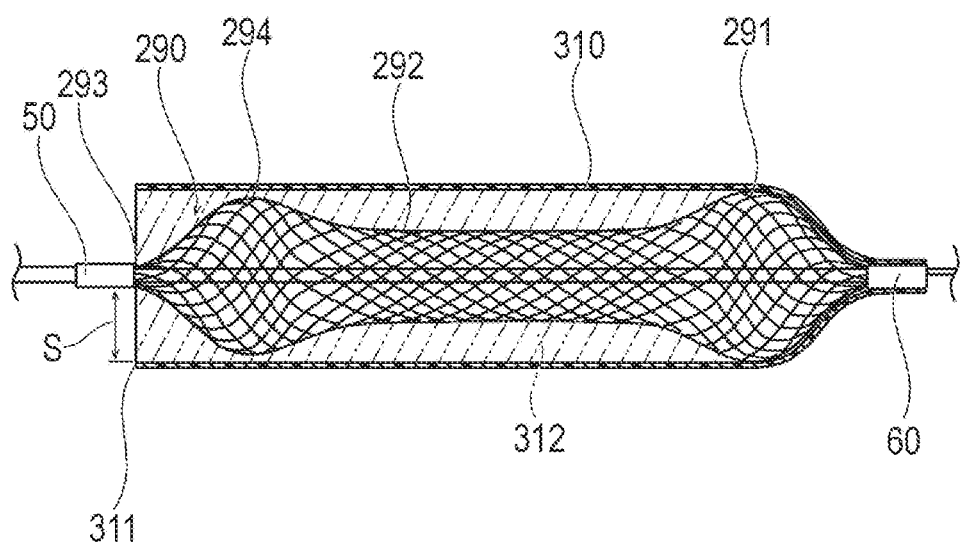

MEDICAL DEVICE AND METHOD FOR TREATMENT

CROSS-REFERENCE TO RELATED APPLICATION

This application claims priority to Japanese Application No. 2016-031781 filed on Feb. 23, 2016, the entire content of which is incorporated herein by reference.

TECHNICAL FIELD

The present disclosure relates to a medical device and a method for treatment, the medical device being intended to remove an object from inside the lumen of the living body.

BACKGROUND DISCUSSION

There occasionally arises pains or tumors when a vein is partly clogged with a thrombus. One method of treatment for such troubles is by the removal of thrombi through a thrombus-removing device which is inserted percutaneously. This method, however, involves a possibility of causing pulmonary embolism in the case where the thrombus which has entirely or partly peeled off the vascular wall reaches the lung together with the blood flow. A common countermeasure to avoid this trouble is to use a thrombolytic agent before and after treatment and/or during treatment, or to remove by suction as many thrombi as possible during treatment. Such measures, however, still have the possibility that some peeled thrombi large enough to cause clinical problems reach the lung.

One of the known methods for avoiding pulmonary embolism involves the use of a filter to catch and collect thrombi flowing through the blood vessel, as shown in U.S. Pat. No. 8,562,637 for example. This filter takes on a net-like shape, so that it is inserted into the blood vessel while it is contracted and then it is expanded in the blood vessel.

The filter disclosed in U.S. Pat. No. 8,562,637 has difficulties in catching and collecting small thrombi because it expands in the blood vessel, which results in an enlarged mesh size. It also has a disadvantage of requiring a high power in the case where the thrombi caught and collected by the filter are sucked off against the strong blood flow.

SUMMARY

The present disclosure is directed to a medical device and a method for treatment. The medical device is easy to operate and the device and the method are capable of effectively removing any substance from inside the lumen of the living body by blocking the flow inside the lumen of the living body.

The medical device according to the disclosure herein is designed to block a fluid flow inside a lumen of a living body when the medical device is inserted into the lumen of the living body. The medical device includes a long shaft part, an expandable part, and a covering part. The expandable part is an elastically deformable cylindrical body with a plurality of pores, which takes on a shape such that its central part becomes larger in outer diameter than its both end parts while it is in its natural state, without external forces, and the cylindrical body has its proximal part connected to the shaft part. The covering part takes on a cylindrical shape surrounding an outer periphery of the expandable part and is flexible and deformable independently of the expandable part. The proximal part of the cylindrical shape is connected to a proximal part of the expandable part or to a member at a proximal side with respect to the expandable part. The covering part includes a space in the radial direction between the distal side end part of the cylindrical shape and the expandable part.

The method for treatment according to the disclosure herein is designed to employ the foregoing medical device in order to remove by suction an object that has occurred in a lesion part in a lumen of a living body. The method includes: pushing out the expandable part and the covering part from the sheath to the downstream side beyond the lesion part in the lumen of the living body, allowing the expandable part to expand by its own elastic force, and causing the covering part to come into contact with the lumen of the living body, while securing a space in the radial direction between the end part of distal side of the covering part and the expandable part; crushing or dissolving the object that has occurred in the lesion part in the lumen of the living body; inserting a device provided with a suction mouth into the lumen of the living body, thereby suctioning the crushed or dissolved object; causing the expandable part and covering part to contract; and pulling the medical device out of the lumen of the living body.

The medical device and the method for treatment, as configured and described-above, produce the following effects. Once the expandable part and the covering part are released from the sheath, the expandable part expands in conformity with the shape of the lumen of the living body by its own elastic force, and this in turn causes the covering part to be pushed against the lumen of the living body by the expandable part. Thus, the covering part effectively blocks the flow in the lumen of the living body and makes it possible to effectively remove any substance from the lumen of the living body. Moreover, the space formed between the distal side end part of the covering part and the expandable part allows the covering part to be pushed against the lumen of the living body only at the proximal side. This facilitates the positioning of the covering part relative to the lumen of the living body, thereby contributing to improved operability. In addition, the space formed between the distal side end part of the covering part and the expandable part decreases the frictional resistance between the covering part and the expandable part; this in turn decreases the resistance which is encountered when the covering part and the expandable part are pushed out of the sheath or housed into the sheath. Hence, improved operability is obtained.

BRIEF DESCRIPTION OF THE DRAWINGS

FIG. 1 is a plan view illustrating a medical device according to an exemplary embodiment of the disclosure;

FIG. 2 is a plan view illustrating the medical device according to the exemplary embodiment, the medical device being composed of an expanding tool, a pressing shaft, and a sheath, which are combined together;

FIGS. 3A and 3B are plan views illustrating a covering part of the expanding tool, FIG. 3A illustrates the covering part in its expanded state, and FIG. 3B illustrates the covering part in its contracted state;

FIGS. 4A and 4B are plan views illustrating an expandable part in the covering part of the expanding tool, FIG. 4A illustrates the expandable part in its expanded state, and FIG. 4B illustrates the expandable part in its contracted state;

FIG. 14A illustrates the state in which the medical device is inserted into the blood vessel, and FIG. 14B illustrates the state in which the medical device, with its expandable part and its covering part being expanded, in the blood vessel;

FIG. 17A illustrates the state in which the medical device, with its sheath and its pressing shaft, being pulled out of the blood vessel, and FIG. 17B illustrates the state in which the medical device, with the removing device, being inserted into the blood vessel;

FIG. 18A illustrates the state of the medical device, with a stirring part of the removing device expanded, and FIG. 18B illustrates the state in which the stirring part crushes a thrombus;

FIGS. 23A and 23B are sectional views illustrating the state in the blood vessel, FIG. 23A illustrates the state in which the thrombus sticking to the expanding tool is being suctioned, and FIG. 23B illustrates the state in which the stirring part is housed into the outermost sheath;

FIGS. 24A and 24B are sectional views illustrating the state in the blood vessel, FIG. 24A illustrates the state in which the removing device has been pulled out of the blood vessel, and FIG. 24B illustrates the state in which the covering part has been housed into the sheath;

FIGS. 25A and 25B are plan views illustrating a modified example of the expandable part of the expanding tool and of the covering part;

FIG. 28 is a plan view illustrating a still further modified example of the expandable part of the expanding tool and of the covering part; and FIG. 29 is a plan view illustrating another modified example of the expandable part of the expanding tool and of the covering part.

DETAILED DESCRIPTION

Figure 5:
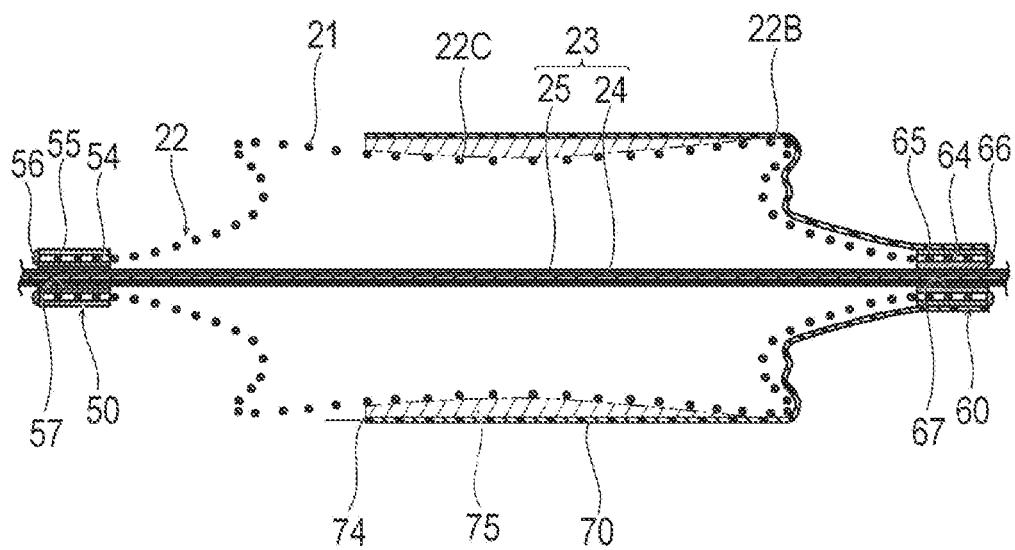
FIG. 5 is an enlarged sectional view illustrating the expandable part and the covering part in their expanded state.

An exemplary embodiment of the disclosure herein will be described below with reference to the accompanying drawings. The scale of the drawings herein may occasionally be different from the actual one because it is exaggerated for the sake of explanation.

A medical device 10 pertaining to an exemplary embodiment of the present disclosure is used to control the flow in a blood vessel so as to remove any object, such as thrombus and plaque, from the blood vessel by suction. The following terms are used in this specification. "Distal side" to denote an insertion side of the medical device which is inserted into the blood vessel; and "proximal side" to denote a hand side of the medical device which is used to operate the medical device. Moreover, the objects to be removed are not necessarily restricted to thrombus and plaque but they include any object which may exist in the lumen of the living body. Also, the following terms are used in this specification. "Upstream side" to denote a side of the blood vessel from which the blood flows; and "downstream side" to denote a side of the blood vessel to which the blood flows.

The medical device 10 according to the exemplary embodiment of the present disclosure includes an expanding tool 20 which blocks the flow of blood in the blood vessel, a sheath 30 which houses the expanding tool 20 therein, and a pressing shaft 40 which pushes out the expanding tool 20 from the sheath 30, as illustrated in FIGS. 1 and 2. As used herein, the blocking of blood flow means closing or diminishing the cross section perpendicular to the axis of the blood vessel and thereby controlling, suppressing, shutting off, or reducing of the blood flow.

The expanding tool 20 includes an expandable part 22 which is a reticulate cylindrical body capable of elastic deformation and has a plurality of pores 21A, a covering part 70 which surrounds the outer periphery of the expandable part 22, and a long shaft part 23 which passes through the expandable part 22 and the covering part 70, as illustrated in FIGS. 3A, 3B, 4A and 4B.

The shaft part 23 includes a long wire part 24 and a tubular body 25 for guide wire, which is fixed to the distal part of the wire part 24 and has a guide wire lumen 26 formed therein, as illustrated in FIGS. 1, 5, 6, and 7. The tubular body 25 for guide wire is fixed to an inner peripheral surface 67 of an inner tube 64 provided at the proximal part of the expandable part 22. The tubular body 25 for guide wire has a through-hole 27 for the wire into which the wire part 24 is inserted and fixed, the through-hole 27 for the wire being formed parallel to the guide wire lumen 26. Further, the wire part 24 may have a distal end 24a thereof fixed to the inner peripheral surface 67 of the inner tube 64 at the proximal part of the expandable part 22. The wire part 24 of the shaft part 23 may be separate from or integral with the tubular body 25 for guide wire.

The wire part 24 constituting the shaft part 23 may be formed suitably from any material, such as stainless steel and shape-memory alloy, without specific restrictions. The tubular body 25 for guide wire, which constitutes the shaft part 23, may be formed suitably from any material without specific restrictions, the material including plastics such as polyimide and polyamide, stainless steel, and shape-memory alloy.

As illustrated in FIGS. 4A, 4B and 5, the expandable part 22 includes a plurality of flexible and deformable wires 21 which are reticularly braided or otherwise intertwined to form a cylindrical body having pores 21A. The expandable part 22 also has a distal side connecting part 50 and a proximal side connecting part 60 which are connected to the tubular body 25 for guide wire of the shaft part 23. The tubular body 25 for guide wire of the shaft part 23 has its outer peripheral surface fixed to the inner peripheral surface 67 of the inner tube 64 of the proximal side connecting part 60. An inner tube 54 of the distal side connecting part 50 has an inner peripheral surface 57 thereof left slidable because the outer peripheral surface of the tubular body 25 for guide wire is not fixed. The expandable part 22 is composed of a plurality of the wires 21 which are braided to form a tubular body in such a way that the pores 21A are formed between the wires 21.

The expandable part 22 is capable of deformation in its natural state in the absence of external force. That is, it takes on an expanded state, with its diameter increased due to elastic force (restoring force) of the wires 21 as illustrated in FIGS. 4A and 5; it also takes on a contracted state, with its outer diameter decreased due to elastic deformation as illustrated in FIG. 4B. The expandable part 22 includes a proximal side tapered part 22A, a proximal side large-diameter part 22B, a small-diameter part 22C, a distal side large-diameter part 22D, and a distal side tapered part 22E. Each of the above parts possesses the following in a natural state in which the expandable part 22 expands due to its own elastic force in the absence of external force. In the proximal side tapered part 22A, internal and external diameters thereof gradually increase toward the distal side from the proximal side connecting part 60. The proximal side large-diameter part 22B and the distal side large-diameter part 22D are both positioned at the distal side of the proximal side tapered part 22A and project outward in the radial direction. The small-diameter part 22C is positioned between the proximal side large-diameter part 22B and the distal side large-diameter part 22D, both being juxtaposed in the axial direction. In the distal side tapered part 22E, internal and external diameters thereof gradually increase toward the proximal side from the distal side connecting part 50. The expandable part 22 in its natural state takes on such a form that the proximal side tapered part 22A and the distal side tapered part 22E are partly depressed toward the inside of the expandable part 22. This structure permits the expandable part 22 to have a large expandable outer diameter, and also permits the expandable part 22 to have a shorter length in the axial direction. The expandable part 22 may have the depression at either the distal side or the proximal side thereof, or both.

The proximal side large-diameter part 22B is positioned between the proximal side tapered part 22A and the small-diameter part 22C, and expands in the radial direction to push the covering part 70 against the inner wall of the blood vessel. The expandable part 22 has a maximum outer diameter larger than the maximum inner diameter of the covering part 70 when it is not covered by the covering part 70 and it expands (to increase in diameter) with the self-expanding force of the expandable part 22. Consequently, the expandable part 22 covered by the covering part 70 is restrained from completely expanding by the covering part 70 when it expands with its own elastic force in its natural state. The expandable part 22 is housed in the sheath 30 so that it takes on a first contracted state. The expandable part 22 also expands in the blood vessel to an extent smaller than the maximum inner diameter of the covering part 70, where it takes on a second contracted state with its further expansion restricted by the blood vessel. Moreover, the expandable part 22 expands in the covering part 70 to the expandable maximum outer diameter, and it takes on a third contracted state with its further expansion being restricted by the covering part 70. The expandable part 22 has an outer diameter which is largest in its expanded state and sequentially decreases in the third contracted state, the second contracted state, and the first contracted state where the outer diameter is smallest.

Figure 6:
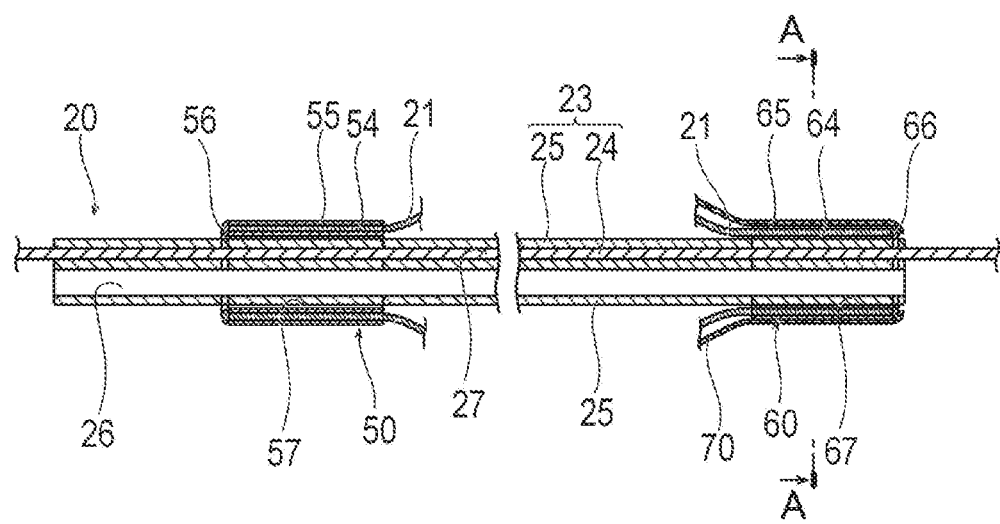
FIG. 6 is an enlarged sectional view illustrating a proximal side connecting part and a distal side connecting part.
Figure 7:
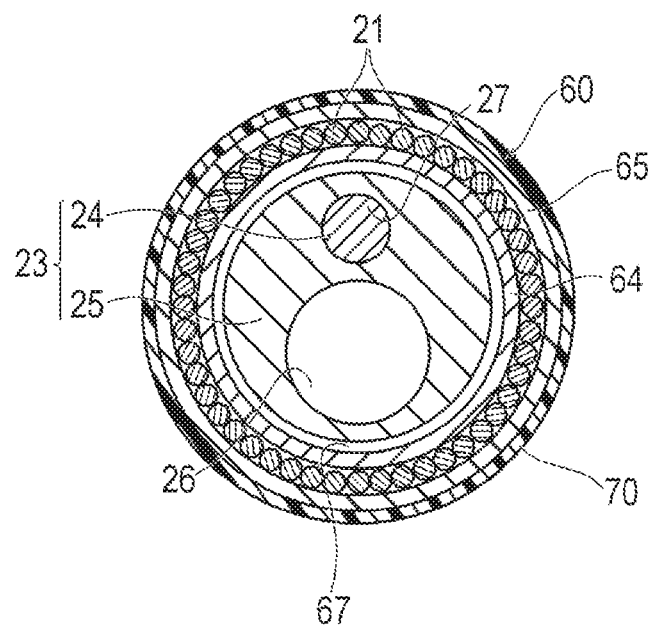
FIG. 7 is a sectional view taken along the line A-A in FIG. 6.

As illustrated in FIGS. 5 to 7, the proximal side connecting part 60 includes the inner tube 64 positioned inside the wires 21, an outer tube 65 positioned outside the wires 21, and a joining part 66 to join together the inner tube 64 and the outer tube 65 at their end parts. The wires 21 are held and fixed between the inner tube 64 and the outer tube 65. The proximal side connecting part 60 has the inner tube 64 fixed to the tubular body 25 for guide wire. It is noted that the joining part 66 may be omitted if the wires 21 can be fixed. Also, the proximal side connecting part 60 may be slidably joined to the shaft part 23. Consequently, the proximal side connecting part 60 may be rotatably joined to the tubular body 25 for guide wire or slidably joined, in the axial direction to a prescribed extent, to the tubular body 25 for guide wire. The proximal side connecting part 60 may be bonded directly to the shaft part 23 or the tubular body 25 for guide wire. The proximal side connecting part 60 is a member joined to the wires 21 and the covering part 70 on the shaft part 23 and the tubular body 25 for guide wire. The joining member may be the inner tube 64 or the outer tube 65 or the joining part 66, or an adhesive. The proximal side connecting part 60 may constitute a portion of the shaft part 23 if it is either fixed to the shaft part 23 or slidably, in a prescribed extent, joined to the shaft part 23.

The distal side connecting part 50 includes the inner tube 54 positioned inside the wires 21, an outer tube 55 positioned outside the wires 21, and a joining part 56 to join together the inner tube 54 and the outer tube 55 at their end parts. The wires 21 are sandwiched to be fixed between the inner tube 54 and the outer tube 55. Since the tubular body 25 for guide wire is slidably inserted into the inside of the inner tube 54, the distal side connecting part 50 has a gap between the inner tube 54 and the tubular body 25 for guide wire, so that it is movable in the axial direction relative to the tubular body 25 for guide wire. As also noted above, in the case where the wires 21 can be fixed, the joining part 56 may be omitted. The gap between the inner tube 54 and the tubular body 25 for guide wire should preferably be 0.01 to 1.0 mm in the exemplary embodiment, but there are no specific restrictions.

The distal side connecting part 50 slides toward the proximal side relative to the tubular body 25 for guide wire and approaches the proximal side connecting part 60 as the expandable part 22 expands (see FIGS. 3A and 4A). Upon contraction, the expandable part 22 slides toward the distal side relative to the tubular body 25 for guide wire and moves away from the proximal side connecting part 60 (see FIGS. 3B and 4B). The fact that the distal side connecting part 50 is capable of coming close to or moving away from the proximal side connecting part 60 allows the braided expandable part 22 to significantly change in its outer diameter.

The wires 21 are not specifically restricted in their number. The number may range from 4 to 72, for example. Also, the wires 21 may be braided or woven in any way without specific restrictions.

The wires 21 may have any outer diameter properly selected according to their material and the use of the expandable part 22. An acceptable diameter ranges from 20 to 300 µm, for example, in the exemplary embodiment.

The wires 21 should preferably include a wire 21B and a wire 21C which are different in outer diameter. The wire 21B is larger in outer diameter than the wire 21C. The outer diameter of the wire 21B may be 200 µm, for example, and the outer diameter of the wire 21C may be 120 µm, for example. According to the exemplary embodiment disclosed herein, two strands of the wire 21B and one strand of the wire 21C are alternatively arranged. Thus, sixteen strands of the wire 21B and eight strands of the wire 21C are employed. The fact that the expandable part 22 includes the wire 21B and the wire 21C, which differ in outer diameter, allows the thin wire 21C not to easily come into contact with the inner wall of the sheath 30 through the covering part 70 when the expandable part 22 is contracted and housed in the sheath 30. Consequently, this structure prevents the intersections of the braid or interwoven mesh from displacing easily, which helps stabilize the shape of the expandable part 22. If there are more of the thick wires 21B than thin wires 21C, the expandable part 22 maintains a greater expanding force and keeps its shape stable. However, the number of thick wires may be smaller than or equal to the number of thin wires. If the number of thick wires is less than the number of thin wires, the expandable part will be more flexible and easy to conform to the shape of the lumen of the living body.

The wires 21 should preferably be made of any one of the flexible materials including: shape-memory alloy which is given the shape-memory effect or superelasticity upon heat treatment; stainless steel; tantalum (Ta); titanium (Ti); platinum (Pt); gold (Au); tungsten (W); polyolefin such as polyethylene and polypropylene; polyamide; polyester such as polyethylene terephthalate; fluorine polymer such as tetrafluoroethylene-ethylene copolymer (ETFE); polyether ether ketone (PEEK), and polyimide. Preferable shape-memory alloys include Ni—Ti alloys, Cu—Al—Ni alloys, and Cu—Zn—Al alloys, which may be used in combination with one another. The wires 21 may also be formed from a plurality of materials combined together. They may have such a structure for imparting a radiopacity that the core wire of Pt is coated with Ni—Ti alloy, or the core wire of Ni—Ti alloy is coated with gold plating.

The outer tubes 55 and 65 are not specifically restricted in outer diameter. Typical values range from 0.3 to 3.0 mm, for example. The inner tubes 54 and 64 are also not specifically restricted in inner diameter and, for example, typical values range from 0.1 to 2.0 mm.

The inner tubes 54 and 64 and the outer tubes 55 and 65 may be formed from any material without specific restrictions. Preferable materials include stainless steel and shape-memory alloy.

The expandable part 22 preferably has a maximum outer diameter which is appropriately selected according to the inner diameter of the blood vessel to which the medical device is to be applied. Typical values range from 1 to 40 mm, for example. The expandable part 22 in its contracted state also preferably has an outer diameter properly selected according to the inner diameter of the blood vessel to which the medical device is to be applied. Typical values range from 0.3 to 4.0 mm, for example. The expandable part 22 in its contracted state may have a length in the axial direction that is selected according to the blood vessel to which the medical device is to be applied. Typical values range from 20 to 150 mm, for example, in the exemplary embodiment.

Figure 8:
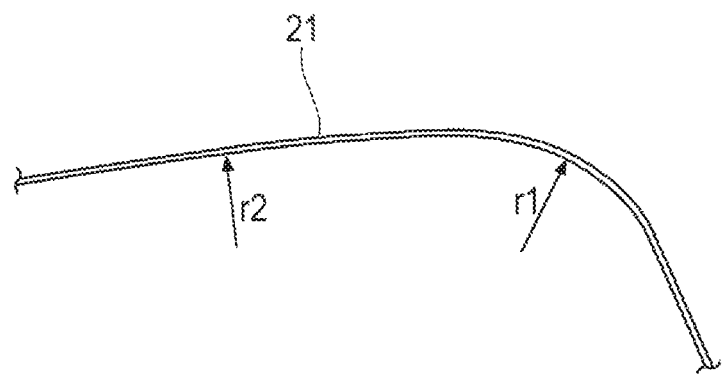
FIG. 8 is a plan view illustrating one of the wires constituting the expandable part.
Figure 9:
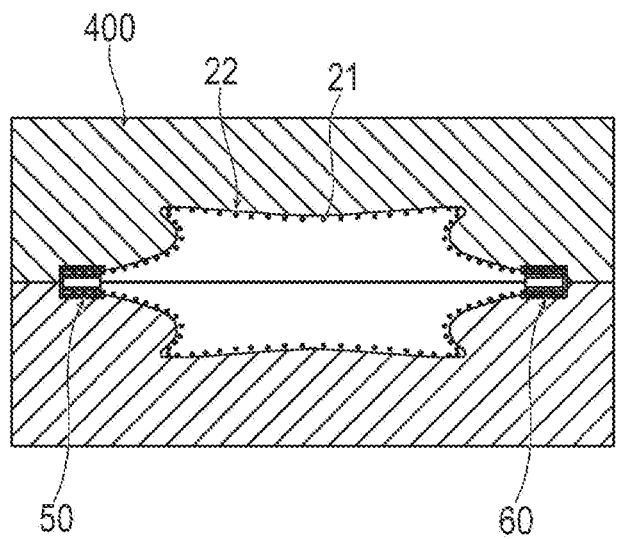
FIG. 9 is a sectional view illustrating the mold to form the expandable part of the exemplary embodiment.

The expandable part 22 is composed of the wires 21. Each of the wires 21 in its natural state without external force acting thereon has a curvature radius which varies depending on a site thereof, as illustrated in FIG. 8. That is, the wire constituting the proximal side large-diameter part 22B and the distal side large-diameter part 22D has a curvature radius r1 that is smaller than a curvature radius r2 at a site constituting the small-diameter part 22C of the wire. The wire as a single constituting member in its natural state without external force acting thereon denotes a single wire which is extracted from the wires 21 of the expandable part 22, as illustrated in FIG. 8. The wires 21 are braided in such a way that the proximal side large-diameter part 22B and the distal side large-diameter part 22D curve to form the projecting parts which point outward in the radial direction of the expandable part 22. Owing to braiding in this manner, the expandable part 22 permits the proximal side large-diameter part 22B and the distal side large-diameter part 22D to project in the radial direction. Moreover, the expandable part 22 is formed by braiding in such a way that the part constituting the small-diameter part 22C curves and projects and faces inward in the radial direction of the expandable part 22. As a result, the expandable part 22 may also permit the proximal side large-diameter part 22B and the distal side large-diameter part 22D to project in the radial direction. The expandable part 22 having the proximal side large-diameter part 22B and the distal side large-diameter part 22D mentioned above may be formed from a shape-memory alloy which produces the shape-memory effect when the material for the wires 21 undergoes heat treatment. This heat treatment may be accomplished by using a mold 400, illustrated in FIG. 9, which has a cavity whose shape conforms to the proximal side large-diameter part 22B and the distal side large-diameter part 22D. To carry out heat treatment, the braided expandable part is housed in the mold 400, which is subsequently heated to a temperature high enough to produce the shape-memory effect. In this way, it is possible to produce the expandable part 22 having the proximal side large-diameter part 22B and the distal side large-diameter part 22D.

Figure 10:
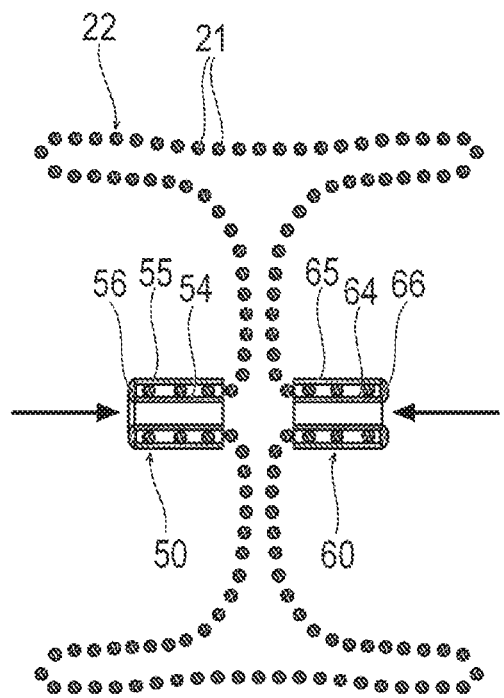
FIG. 10 is a sectional view illustrating how the expandable part is formed.

The foregoing method that employs a mold may be replaced by another method which includes producing the wires 21 from a shape-memory alloy by heat treatment in the following manner, as illustrated in FIG. 10. During heat treatment, the wires 21 are fixed in such a way that the distal side connecting part 50 and the proximal side connecting part 60 are brought close to each other with both ends of the expandable part depressed. This heat treatment involves heating up to a temperature high enough to produce the shape-memory effect. The foregoing method permits the production of the expandable part 22 which forms the proximal side large-diameter part 22B and the distal side large-diameter part 22D when the distal side connecting part 50 and the proximal side connecting part 60 are separated from each other.

The covering part 70 is a tubular member which is formed from a thin film so as to cover the outer periphery of the expandable part 22, as illustrated in FIGS. 3A and 3B. The covering part 70 includes: a cover proximal part 71 which is fastened to the outer periphery of the proximal side connecting part 60; a proximal side tapered part 72 which gradually increases in inner diameter and outer diameter as the proximal side tapered part 72 extends from the cover proximal part 71 toward the distal side; and a cover distal part 73 which is positioned at the distal side of the proximal side tapered part 72 and has an almost constant outer diameter. In the exemplary embodiment, the covering part 70 is only fastened to the expandable part 22 at the cover proximal part 71. The proximal side tapered part 72 and the cover distal part 73 are not fastened to the expandable part 22 but they merely cover the expandable part 22. Therefore, the covering part 70, except for the cover proximal part 71, is capable of deformation independently from the expandable part 22 and is separate from the expandable part 22 without contact with the covering part 70. Consequently, the expandable part 22 and the covering part 70 come into contact with each other at different positions depending on the time of expansion and contraction. In addition, in order for the covering part 70 to be capable of deformation independently of the expandable part 22, the wires 21 constituting the expandable part 22 can vary in crossing angle thereof without interference from the covering part 70. Thus, the expandable part 22 is capable of flexible deformation. Moreover, the expandable part 22 varies in its outer diameter while allowing the wires 21 to change in crossing angle. Therefore, the expandable part 22 decreases in length in the axial direction as it expands in the radial direction, whereas the covering part 70 varies less in its length in the axial direction than the expandable part 22 because the covering part 70 is made of a thin and strong material resistant to breakage. The covering part 70 may also be connected to the shaft part 23 which is a member of the proximal side with respect to the proximal side connecting part 60, rather than connected to the proximal side connecting part 60.

Upon contraction, the covering part 70 contracts or reduces in diameter in such a way as to form folds 77 with the material thereof piling up on each other, as illustrated in FIG. 3B. The folds 77 form into a wrinkled shape and have their edges extended in the axial direction. Also, the folds 77 occur in a plural number in the circumferential direction. The folds 77 do not form themselves over the entire length of the covering part 70 in the axial direction but form themselves intermittently over a length shorter than the entire length in the axial direction of the covering part 70. The intermittently formed folds 77 should preferably exist in a plural number in the axial direction. Incidentally, the individual parts of the folds 77 may extend over the entire length in the axial direction of the covering part 70.

In addition, the covering part 70 expands or increases in diameter in such a way that the folds 77 extend and their superimposed parts decrease in number, as illustrated in FIGS. 3A and 5. In other words, the covering part 70 forms the folds 77 in such a way that the folds 77 are superimposed in the circumferential direction with their inner peripheral surfaces touching one another. Alternatively, the covering part 70 changes in its outer diameter as the folds 77 extend. The covering part 70 may also be constructed such that the folds 77 do not completely extend at the time of its expansion but rather, the folds 77 remain partly unstretched. The covering part 70 is constructed such that the inner peripheral surface of the cover distal part 73 of the covering part 70, the cover distal part 73 having the inner and outer diameters being uniform, comes into contact with the proximal side large-diameter part 22B of the expandable part 22. The covering part 70 has a distal side end part 74 which is positioned outside in the radial direction of the small-diameter part 22C of the expandable part 22, so that there exists a gap between the distal side end part 74 and the small-diameter part 22C. When the covering part 70 and the expandable part 22 expand from their contracted state, the expandable part 22 decreases in length in the axial direction, and hence the distal side end part 74 of the covering part 70 moves toward the proximal side relative to the expandable part 22.

A cylindrical space 75 is formed between the covering part 70 and the expandable part 22, the cylindrical space 75 ranging from that position where the covering part 70 comes into contact with the proximal side large-diameter part 22B to the distal side end part 74 of the covering part 70, as illustrated in FIG. 5.

The covering part 70 plays a role in blocking the blood flow so that the removing device 100, mentioned later, can effectively suction and remove thrombi from the blood vessel.

The covering part 70 has a maximum inner diameter which is smaller than the maximum outer diameter of the expandable part 22 in its expanded state without being covered with the covering part 70. In other words, the covering part 70 surrounds the expandable part 22 so as to prevent the expandable part 22 from expanding. Therefore, this permits the expandable part 22 to effectively produce its expanding force even when the covering part 70 is in its expanded state. The covering part 70 has a maximum outer diameter, which is smaller than the inner diameter of the blood vessel to which the medical device is applied, when the cover distal part 73 of the covering part 70 expands, so as to ensure contact with the inner wall of the blood vessel to which the medical device is applied.

The cover distal part 73 of the covering part 70 may have a maximum outer diameter in the expanded state which is larger than the inner diameter of the blood vessel to which the medical device is applied, and the maximum outer diameter may be properly selected according to the blood vessel to which the medical device is to be applied. Typical values range from 1 to 40 mm, for example. The covering part 70 may have a maximum outer diameter in the contracted state which is smaller than the inner diameter of the blood vessel to which the medical device is applied, and the maximum outer diameter may be properly selected according to the blood vessel to which the medical device is applied. Typical values range from 0.3 to 4.0 mm, for example. The expandable part 22 has a length in the axial direction in the contracted state which can be properly selected according to the blood vessel to which the medical device is applied. Typical values range from 20 to 150 mm, for example.

The covering part 70 should preferably be made of a material which has strength high enough to resist breakage at the time of deformation, and which has frictional resistance low enough to permit sliding in the sheath 30. Such a material includes polyethylene, for example. The covering part 70 may have a thickness ranging from 5 to 30 µm, in the exemplary embodiment, for example, without specific restrictions thereto.

The covering part 70, instead of being a film-like member, may be a mesh-like film member or a braided member prepared from wires by braiding.

The covering part 70 may have its inner surface coated with a silicone resin, fluorine resin such as Teflon®, or hydrophilic polymer for improved slidability. Examples of the hydrophilic polymer include polyhydroxyethyl methacrylate, polyhydroxyethyl acrylate, hydroxypropyl cellulose, methyl vinyl ether-maleic anhydride copolymer, polyethylene glycol, polyacrylamide, and polyvinyl pyrrolidone.

The inner surface with improved slidability permits the covering part 70 to be easily retracted into the sheath 30 after the covering part 70 has been expanded in the blood vessel. The treatment for improved slidability may be applied to not only the inner peripheral surface of the covering part 70 but also the outer peripheral surface of the covering part 70 excluding the area of the cover distal part 73 which needs a force for contact with the wall of the blood vessel. The thus treated surface permits the covering part 70 to be easily retracted into the sheath 30 after the covering part 70 has been expanded in the blood vessel.

The sheath 30, illustrated in FIGS. 1 and 2, includes a sheath tubular body 31, a hub 32, and a kink-resistant protector 33. The sheath tubular body 31 has a lumen 34 in which the expanding tool 20 is housed, and the sheath tubular body 31 opens at a tube opening part 36 formed at the distal side end part thereof. The hub 32 is fixed to the proximal side end part of the sheath tubular body 31, and it has the hub opening part 35 communicating with the lumen 34. The kink-resistant protector 33 is a flexible member that covers a connecting part of the sheath tubular body 31 and the hub 32, and protects the sheath tubular body 31 from kinking.

The sheath tubular body 31 may be formed from any material without specific restrictions. Typical examples which can be suitably used include: polyolefins such as polyethylene, polypropylene, ethylene-propylene copolymer, and ethylene-vinyl acetate copolymer; polyvinyl chloride; polystyrene; polyamide; polyimide; and a combination thereof. The sheath tubular body 31 may be formed from more than one material or may have a reinforcing material such as wire embedded therein.

The pressing shaft 40 is a tubular body and housed in the lumen 34 of the sheath 30. The pressing shaft 40 has a pushing lumen 41 formed thereon, into which the wire part 24 of the expanding tool 20 is inserted. The pushing lumen 41 has an inner diameter which is smaller than the outer diameter of the proximal side connecting part 60 of the expanding tool 20. Therefore, the proximal side connecting part 60 cannot enter the pushing lumen 41, and hence this permits the pressing shaft 40 to push the proximal side connecting part 60 toward the distal direction.

The following description is concerned with the removing device 100 which is designed to remove thrombi by insertion into the blood vessel.

Figure 11:
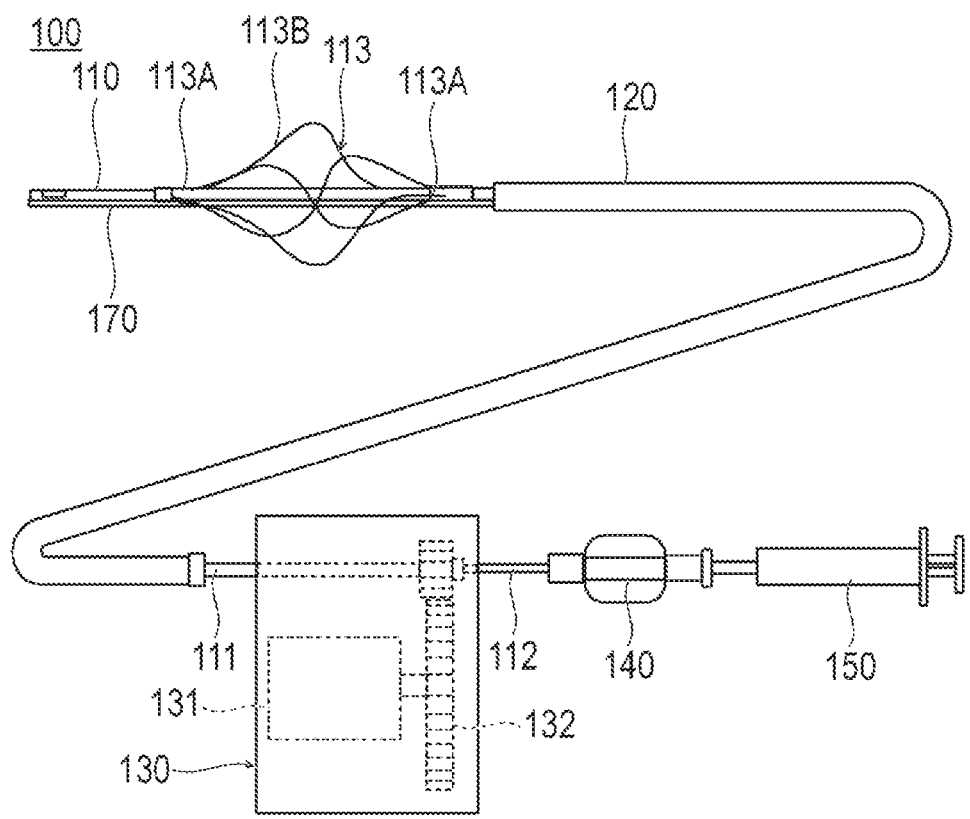
FIG. 11 is a plan view illustrating a removing device according to an exemplary embodiment.
Figure 12:
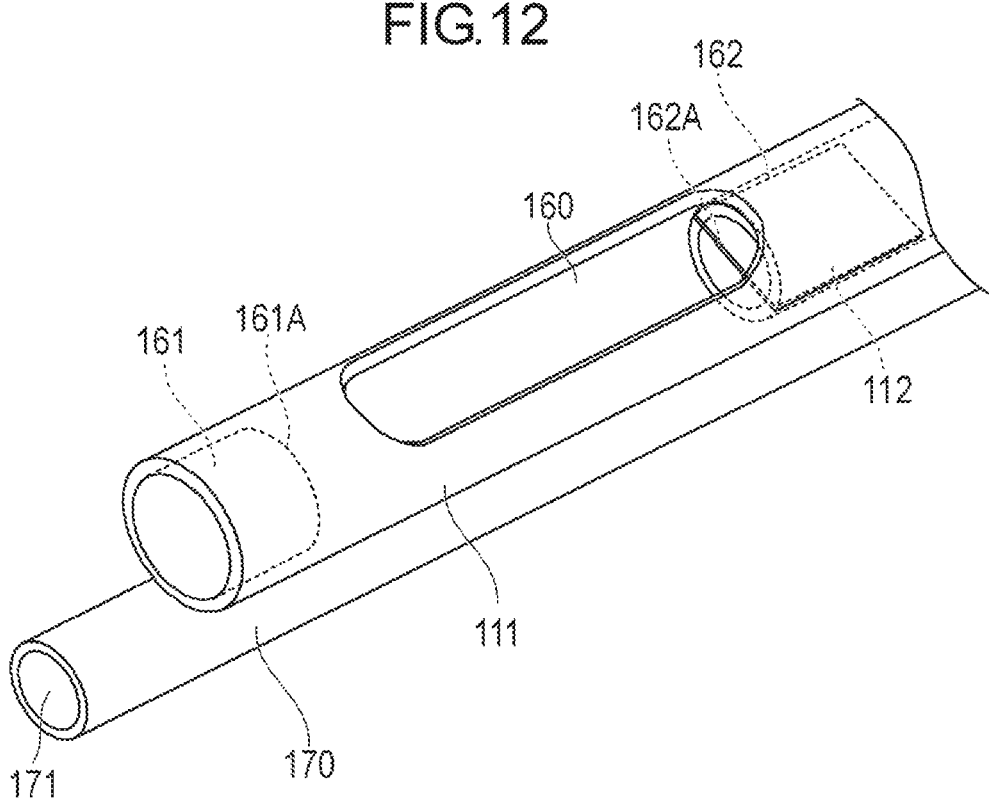
FIG. 12 is a perspective view illustrating the distal part of the removing device.
Figure 13:
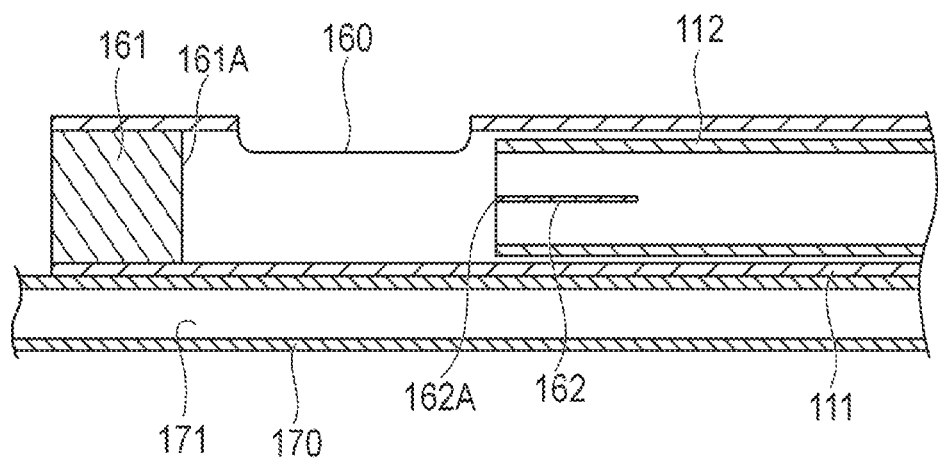
FIG. 13 is a sectional view illustrating the distal part of the removing device.

The removing device 100, as illustrated in FIGS. 11 to 13, includes a shaft main body 110 which is formed long, an outermost sheath body 120 which houses the shaft main body 110 therein and is slidable in the axial direction relative to the shaft main body 110, and a tubular body 170 for guide wire in which a second guide wire lumen 171 is formed. The removing device 100 additionally has a rotary drive part 130 which rotates the shaft main body 110, the hub 140 which is provided at the proximal side end part of the shaft main body 110, and a syringe 150 connected to the proximal side of the hub 140.

The shaft main body 110 includes a shaft outer tube 111 and a shaft inner tube 112, which are formed in a long and hollow shape. The shaft outer tube 111 and the shaft inner tube 112 have their respective inner lumens. The inner diameter of the shaft outer tube 111 is larger than the outer diameter of the shaft inner tube 112, so that the shaft inner tube 112 is housed in the hollow part of the shaft outer tube 111. In addition, the shaft inner tube 112 is movable relative to the shaft outer tube 111 in the axial direction thereof.

The shaft outer tube 111 has a distal side end part that forms the distal part of the shaft main body 110, and also has a proximal side end part at which is placed the rotary drive part 130. The shaft inner tube 112 has a proximal side end part which extends toward the proximal side further than the proximal side end part of the shaft outer tube 111, and which is connected to the hub 140. The syringe 150 connected to the hub 140 evacuates the hollow part of the shaft inner tube 112 by suction to generate a negative pressure state in the hollow part.

The tubular body 170 for guide wire is positioned around and fixed to the shaft outer tube 111. The tubular body 170 for guide wire has the second guide wire lumen 171 which permits the guide wire to be inserted.

The shaft outer tube 111 is made of a material which is flexible and capable of transmitting the rotating power acting on the proximal side to the distal side. The shaft inner tube 112 is made of a material which is flexible and capable of transmitting the reciprocating power acting on the proximal side to the distal side. For example, the shaft outer tube 111 and the shaft inner tube 112 may be formed from a multi-layered, including three-layered, tubular body in a coil shape wound in alternating directions, which is made of polyolefin such as polyethylene and polypropylene, polyamide, polyester such as polyethylene terephthalate), fluorine polymer such as ethylene-tetrafluoroethylene copolymer (ETFE), polyether ether ketone (PEEK), or polyimide, or a combination thereof. These materials may have a reinforcing member such as a wire embedded therein.

The outermost sheath body 120 may be formed from any material without specific restrictions. Typical preferable examples which can be suitably used include polyolefin such as polyethylene and polypropylene, polyamide, polyester such as polyethylene terephthalate, fluorine polymer such as ethylene-tetrafluoroethylene copolymer (ETFE), polyether ether ketone (PEEK), and polyimide. It may also be formed from a plurality of materials combined together, or a material having reinforcement such as wires embedded therein.

The shaft outer tube 111 is provided with a stirring part 113 at the distal part thereof. The stirring part 113 is connected to the periphery of the shaft outer tube 111 at two bases 113A which are close to the proximal side and distal side. The two bases 113A are bridged by spiral parts 1136. The spiral parts 1136 are twisted in the identical direction to each other along the axial direction. Moreover, the spiral parts 1136 are fixed at positions different to each other in the circumferential direction and bend to different directions along the axial direction. Consequently, the stirring part 113 as a whole is formed such that it uniformly bulges in the circumferential direction. When the shaft outer tube 111 rotates, the stirring part 113 also rotates with it, so that it crushes thrombi in the blood vessel or stirs crushed thrombi.

The spiral parts 113B of the stirring part 113 are formed from flexible thin metal wires. The stirring part 113 remains held inside the outermost sheath 120 until the shaft main body 110 is inserted into the desired site. After the shaft main body 110 has been inserted into the desired site, the outermost sheath body 120 is slid to the proximal side, so that the stirring part 113 exposes itself outward of the outermost sheath 120 and expands to have a shape illustrated in FIG. 11. Accordingly, the spiral parts 1136 should preferably be formed from a shape-memory material. An adequate material which can be suitably used for the spiral parts 1136 includes a shape-memory alloy which acquires shape-memory effect and super-elasticity upon heat treatment, and stainless steel. Preferable examples of the shape-memory alloy include those of Ni—Ti, Cu—Al—Ni, and Cu—Zn—Al, and a combination thereof.

The rotary drive part 130 includes a drive motor 131 and a gear part 132 which connects the drive motor 131 to the shaft outer tube 111 of the shaft main body 110. The drive motor 131 rotates to turn the shaft outer tube 111 in its circumferential direction. According to the exemplary embodiment, the drive motor 131 rotates so as to turn the shaft outer tube 111 in its mutually opposite directions alternately. As the result of the shaft outer tube 111 turning in its mutually opposite directions alternately, the blood flow changes in its direction alternately.

The shaft outer tube 111 has an opening part 160 having an elongate hole shape in the axial direction, the opening part 160 being formed near the distal part of the shaft outer tube 111. This opening part 160 permits the inner and outside of the shaft outer tube 111 to communicate with each other. The shaft outer tube 111 has a cylindrical attachment part 161 at the distal part thereof so as to block the hollow part of the shaft outer tube 111 to close the distal part of the shaft outer tube 111. The attachment part 161 has an attachment face 161A as a proximal face thereof, the attachment face 161A facing a distal face of the shaft inner tube 112. The attachment face 161A is positioned at the distal side with respect to the distal side end part of the opening part 160 of the shaft outer tube 111. The attachment part 161 may be formed from stainless steel or the like.

The shaft inner tube 112 has a distal side end face which is positioned at the proximal side end part of the opening part 160 of the shaft outer tube 111 or at the proximal side with respect to the proximal side end part of the opening part 160. The cutting part 162 is provided in the hollow part and at the distal side end part of the shaft inner tube 112. The cutting part 162 is formed from a thin metal plate and has a width equivalent to the diameter of the shaft inner tube 112. The cutting part 162 also has the sharp blade 162A at the distal part thereof.

As illustrated in FIG. 12, the blade 162A is arranged such that there is no step between the distal side end face of the blade 162A and the distal side end face of the shaft inner tube 112. Therefore, if the distal face of the shaft inner tube 112 comes into contact with the attachment face 161A of the attachment part 161, the blade 162A also comes into contact with the attachment face 161A. The shaft inner tube 112 moves back and forth in the axial direction along the axis direction over a distance from at least the position illustrated in FIG. 13 to the position at which the shaft inner tube 112 comes into contact with the attachment face 161A of the attachment part 161, with respect to the shaft outer tube 111. The distal part of the shaft inner tube 112 may be thinner than those parts other than the distal part of the shaft inner tube 112 (the thickness equivalent to difference between the outer diameter of the inner tube and the inner diameter of the inner tube), and it may be as thin as the blade 162A of the cutting part 162.

The distal side end face of the blade 162A may project from the distal side end face of the shaft inner tube 112. In the exemplary embodiment, the length of projection should preferably be 0.5 to 100 μm. Projection in this manner permits the blade 162A to effectively act on the attachment face 161A of the attachment part 161, which leads to effective cutting.

The shaft outer tube 111 and the shaft inner tube 112 are coaxially arranged, so that the shaft outer tube 111 can be rotated back and forth in the circumferential direction by the rotary drive part 130. However, the shaft outer tube 111 may be one which rotates in one direction instead of one which rotates back and forth. The cutting part 162 is arranged in such a way that it divides into two parts the sectional area of the hollow part of the shaft inner tube 112.

The following is a description of the method of using the medical device 10 and the removing device 100 according to the exemplary embodiment. The description illustrates the removal of thrombi by suction from the blood vessel.

In the first step, an introducer sheath (not shown) is inserted percutaneously into the blood vessel at the position upstream (proximal side or periphery side) side of the thrombus 300 in the blood vessel. The introducer sheath permits a guide wire 80 to be inserted into the blood vessel. The guide wire 80 is advanced to the distal side of the thrombus 300.

In the second step illustrated in FIG. 2, the medical device 10 is prepared for use, with the sheath 30 housing therein the expanding tool 20 and the pressing shaft 40. The expandable part 22 is arranged at the position near the distal side end part of the sheath tubular body 31 of the sheath 30; it is constrained in the contracted state. The shaft part 23 projects toward the proximal side from the hub opening part 35 of the hub 32.

Figure 14:
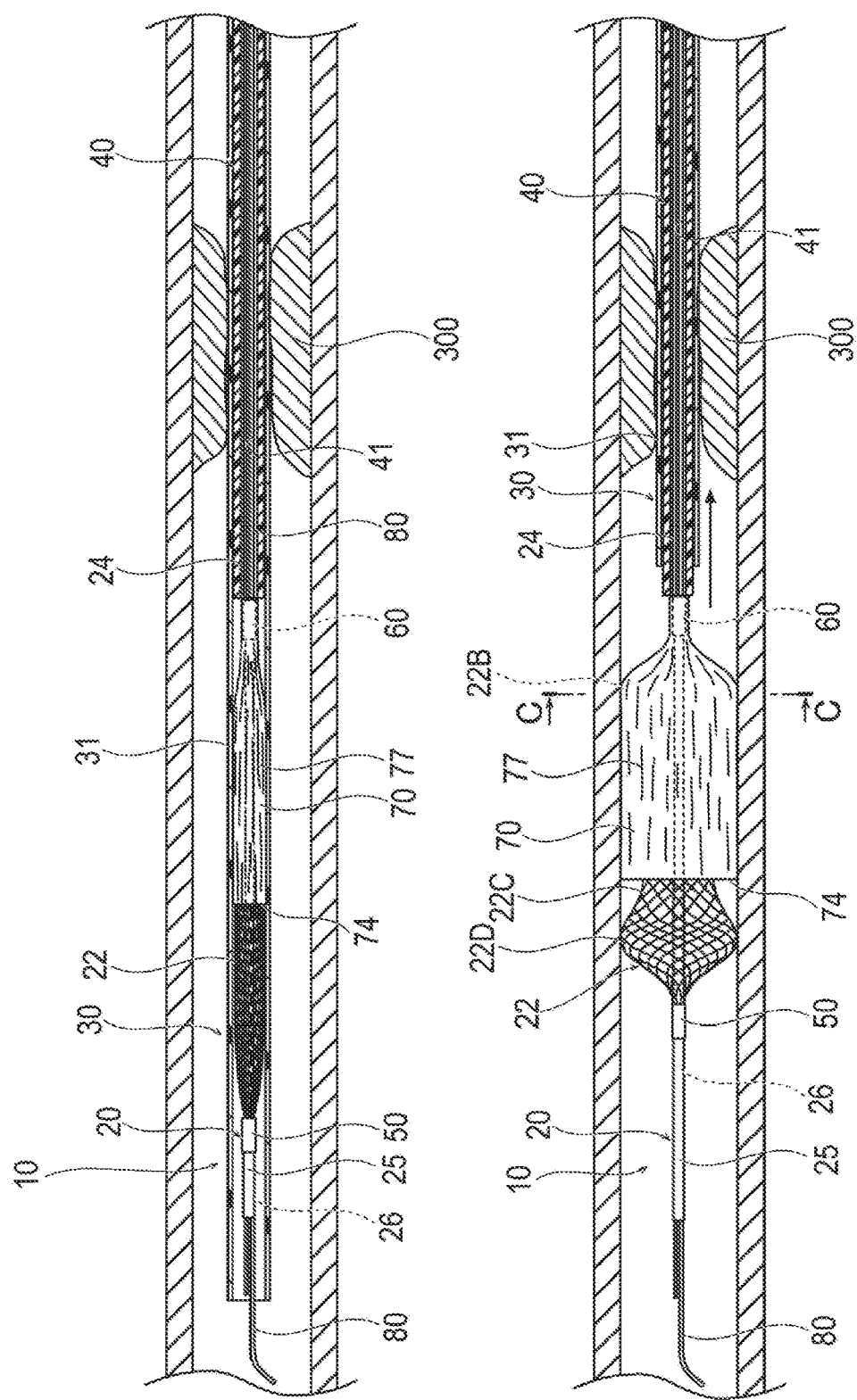
FIGS. 14A and 14B are partial views illustrating the state in the blood vessel.

In the third step, the proximal side end part of the guide wire 80 which is outside the patient's body is inserted into the guide wire lumen 26 of the medical device 10. As illustrated in FIG. 14A, the medical device 10 is advanced to the distal side of the thrombus 300 along the guide wire 80. To advance the guide wire 80 to the distal side of the thrombus 300, a support catheter that is separately provided may be used.

Figure 15:
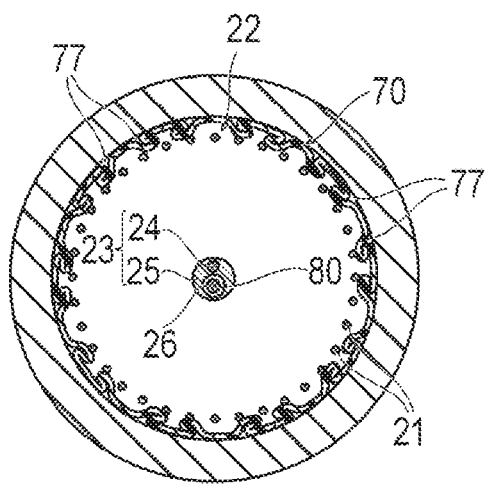
FIG. 15 is a sectional view taken along the line C-C in FIG. 14.

Subsequently, the sheath 30 is moved toward the proximal side, with the pressing shaft 40 kept immobile by holding with the hand. During this step, the distal side end part of the pressing shaft 40 comes into contact with the proximal side connecting part 60 or the proximal side end part of the tubular body 25 for guide wire. Because the expandable part 22 and the covering part 70 are kept immobile, it is possible to adjust as desired the positions of the expandable part 22 and the proximal part of the covering part 70 in the blood vessel. As the sheath 30 moves toward the proximal side relative to the pressing shaft 40, the expandable part 22 and the covering part 70 are released from the sheath tubular body 31. As the result, the distal side connecting part 50 moves so as to approach the proximal side connecting part 60, the expandable part 22 expands to an optimal size by its own restoring force, and the covering part 70 is pressed against the inner wall of the blood vessel by the proximal side large-diameter part 22B so that it is properly positioned, as illustrated in FIG. 14B. Thus, the expandable part 22 which is formed into a mesh shape can be firmly fixed to the inner wall of the blood vessel with the covering part 70 pressed into the inner wall of the blood vessel. Particularly, the distal side large-diameter part 22D, which is not covered with the covering part 70, is firmly fixed to the inner wall of the blood vessel without slipping. Since the folds 77 are stretched and expanded by the expandable part 22 in conformity with the inner diameter and the shape of the blood vessel, the covering part 70 is pressed against and comes into contact with the inner wall of the blood vessel by the expandable part 22. Further, the covering part 70 in contact with the inner wall of the blood vessel does not form any gap between it and the blood vessel even though the folds 77 partly remain because the covering part 70 is pressed against the inner wall of the blood vessel by the expandable part 22, as illustrated in FIG. 15. Since the folds 77 on the covering part 70 are formed short intermittently in the axial direction, they give rise to minute gaps between the folds 77 and the inner wall of the blood vessel which are also formed short intermittently in the axial direction and are not formed continuously in the axial direction. Consequently, the covering part 70 effectively blocks the blood flow.

Figure 16:
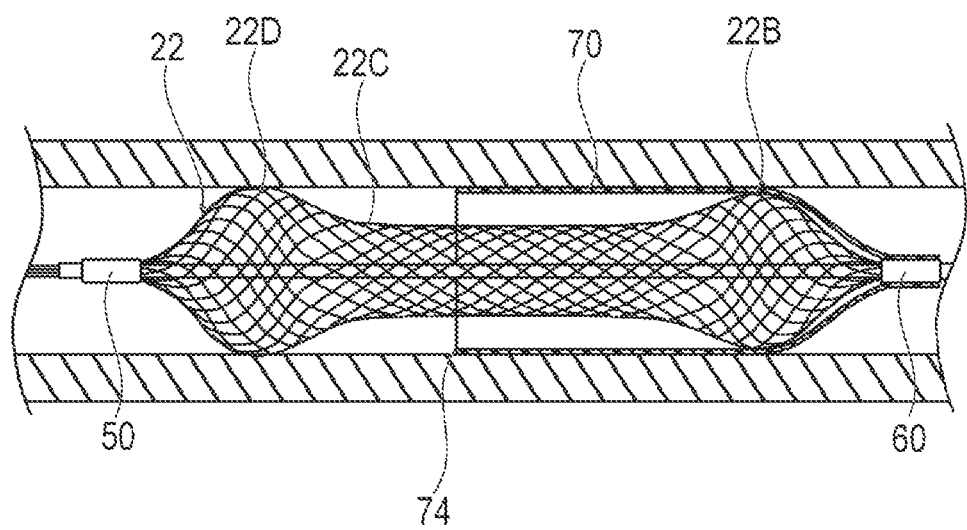
FIG. 16 is a sectional view illustrating the expandable part and the covering part which have been expanded in the blood vessel.
Figure 17:
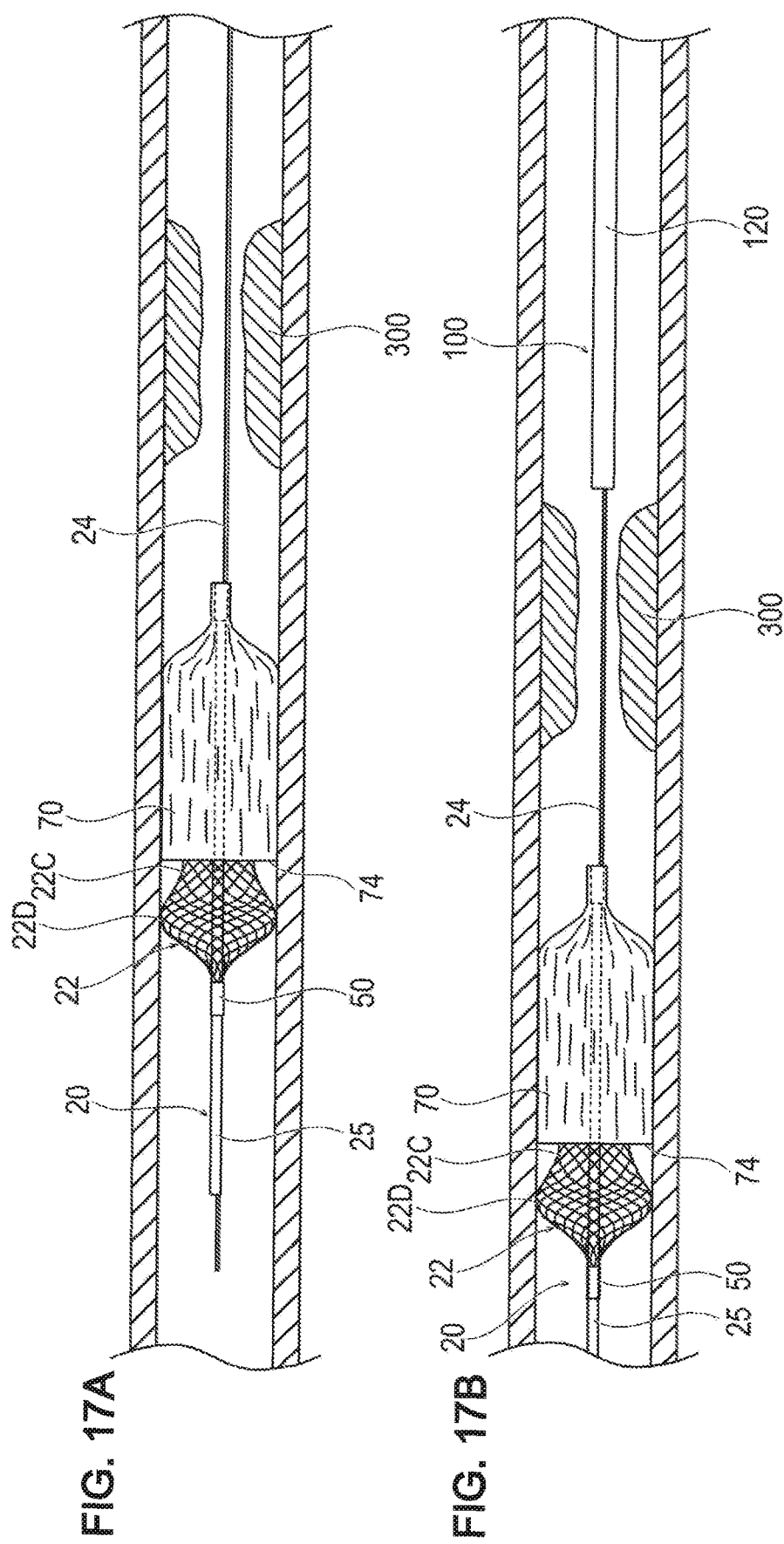
FIGS. 17A and 17B are sectional views illustrating the state in the blood vessel.

Since the maximum diameter to be achieved by expansion of the expandable part 22 is larger than the diameter of the blood vessel into which it is inserted, the expandable part 22 does not expand completely inside the blood vessel but generates expanding force, thereby allowing the covering part 70 to effectively come into close contact with the wall of the blood vessel. Thus, the covering part 70 is pressed against the inner wall of the blood vessel by the proximal side large-diameter part 22B of the expandable part 22, so that it is fixed to the inside of the blood vessel as illustrated in FIGS. 14B and 16. Subsequently, the sheath 30 and the pressing shaft 40 are pulled out from the patient's body, with the expanding tool 20 remaining in the body as illustrated in FIG. 17A.

Since the expandable part 22 is housed in the covering part 70 with its expanded diameter limited by the covering part 70, it is firmly fixed to the inner wall of the blood vessel with a sufficient expanding force even when it has an expanded large outer diameter not only when it has an expanded small diameter. For this reason, the medical device can be applied to blood vessels broadly ranging in inner diameter.

Since gaps are formed between the distal side end part 74 of the covering part 70 and the expandable part 22, the covering part 70 is pressed against the inner wall of the blood vessel within a limited area at a position of the proximal side of the covering part 70. Thus, when the covering part 70 is pushed out from the sheath 30 by the pressing shaft 40 that presses the proximal side of the covering part 70, the covering part 70 comes into contact with the blood vessel at the position close to the pressing shaft 40. This allows the covering part 70 to be positioned accurately while being adjusted to a desired position.

The fact that a gap is formed between the distal side end part 74 of the covering part 70 and the expandable part 22 helps reduce frictional resistance between the covering part 70 and the expandable part 22. Consequently, when the covering part 70 and the expandable part 22 expand and contract in the radial direction, a smooth sliding action takes place between the covering part 70 and the expandable part 22 which change in length differently from each other in the axial direction. This in turn leads to reduction in resistance which is experienced when the covering part 70 and the expandable part 22 are pushed out from the sheath 30 or housed in the sheath 30, and results in an improved operability.

As soon as the expandable part 22 and the covering part 70 have come into close contact with the inner wall of the blood vessel, the blood flow in the blood vessel is blocked or reduced, so that the blood is held up.

Next, the removing device 100 in which the distal part of the shaft main body 110 including the stirring part 113 has been housed in the outermost sheath body 120 is prepared for use, and the proximal side end part of the wire part 24 is inserted into the second guide wire lumen 171 of the removing device 100. After that, the removing device 100 is inserted into the proximal side of the thrombus 300, with the help of the wire part 24 as guide, as illustrated in FIG. 17B. Then, the outermost sheath body 120 is moved toward the proximal side, so that the stirring part 113 expands in the blood vessel, as illustrated in FIG. 18A.

In the next step, a thrombolytic agent is injected into the vicinity of the thrombus 300 in the blood vessel by way of the outermost sheath body 120, the shaft inner tube 112, or the second guide wire lumen 171 (See FIG. 7). The thus injected thrombolytic agent keeps a high concentration and hence produces a thrombolytic effect, because the blood flow is controlled (blocked or reduced) in the region where the thrombus is formed. However, it is not compulsory to use a thrombolytic agent.

After the stirring part 113 has advanced to the vicinity of the thrombus 300, the shaft outer tube 111 is set to rotation by the rotary drive part 130. The stirring part 113 turns together with the shaft outer tube 111. In this way, the thrombus 300 sticking to the blood vessel is crushed.

Figure 18:
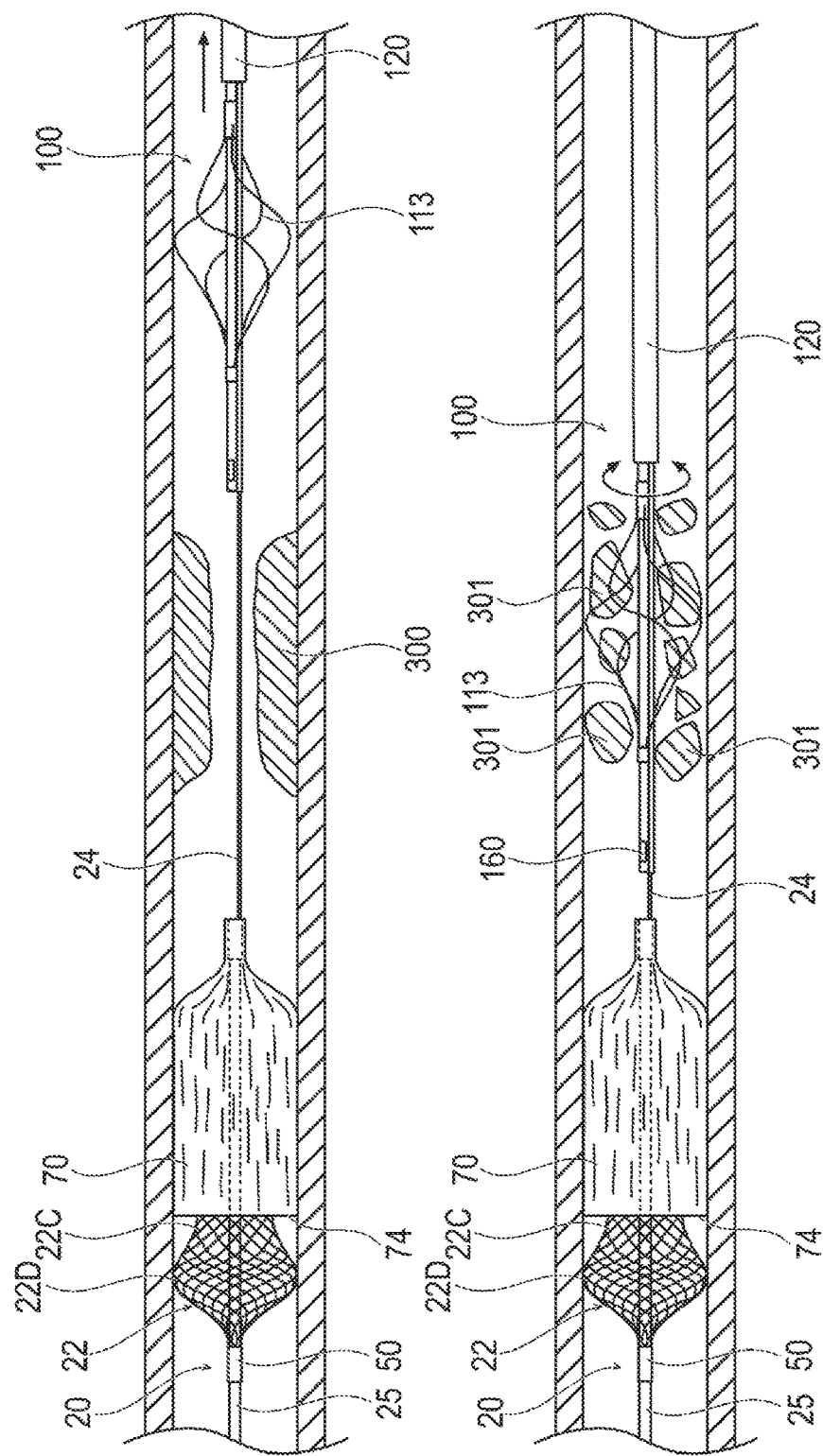
FIGS. 18A and 18B are sectional views illustrating the state in the blood vessel.

The rotating part 113 continues to rotate to crush the entire thrombus 300 sticking to the blood vessel because the blood flow is blocked by the medical device 10, as illustrated in FIG. 18B. The segments 301 of the crushed thrombus float without precipitation in the stagnant blood in the blood vessel.

Figure 19:
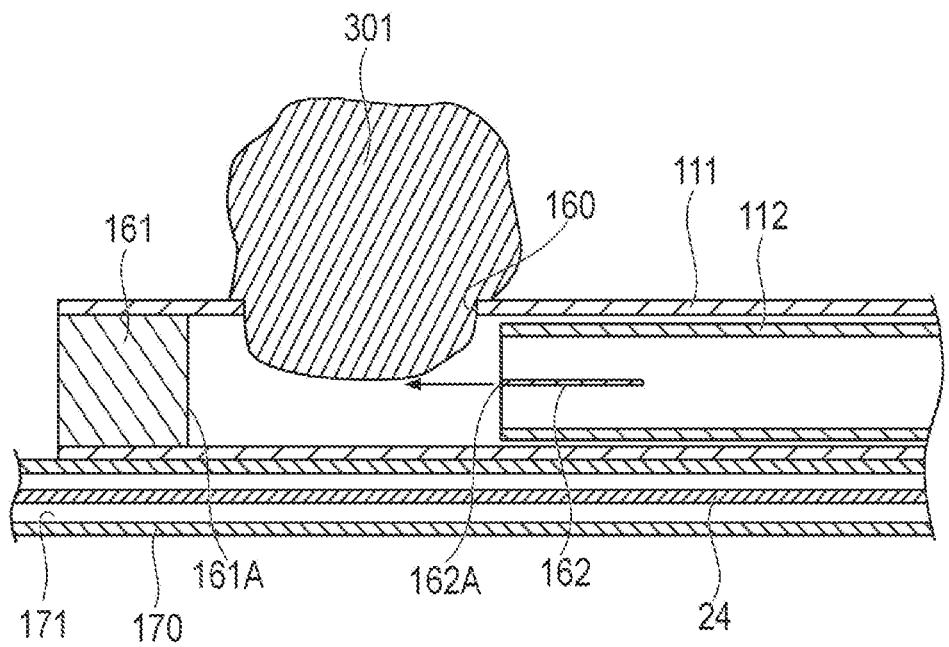
FIG. 19 is an enlarged sectional view illustrating the distal part of the removing device, with the crushed thrombus being suctioned into an opening part of an outer tube.

Then, the plunger of the syringe 150 (illustrated in FIG. 11) is pulled out (drawn) so that the hollow part of the shaft inner tube 112 is evacuated to be a negative pressure state. The distal side end part of the shaft inner tube 112 communicates with the hollow part of the shaft outer tube 111. Moreover, the shaft outer tube 111 also communicates with the outside of the shaft main body 110 through the opening part 160. Therefore, the opening part 160 applies a suction force to the outside of the shaft main body 110 and attracts the segments of the crushed thrombus 300 which are floating in the blood vessel. A remaining thrombus portion 301, which has been attracted to the opening part 160, partly enters the hollow part inside of the shaft outer tube 111, as illustrated in FIG. 19.

Figure 20:
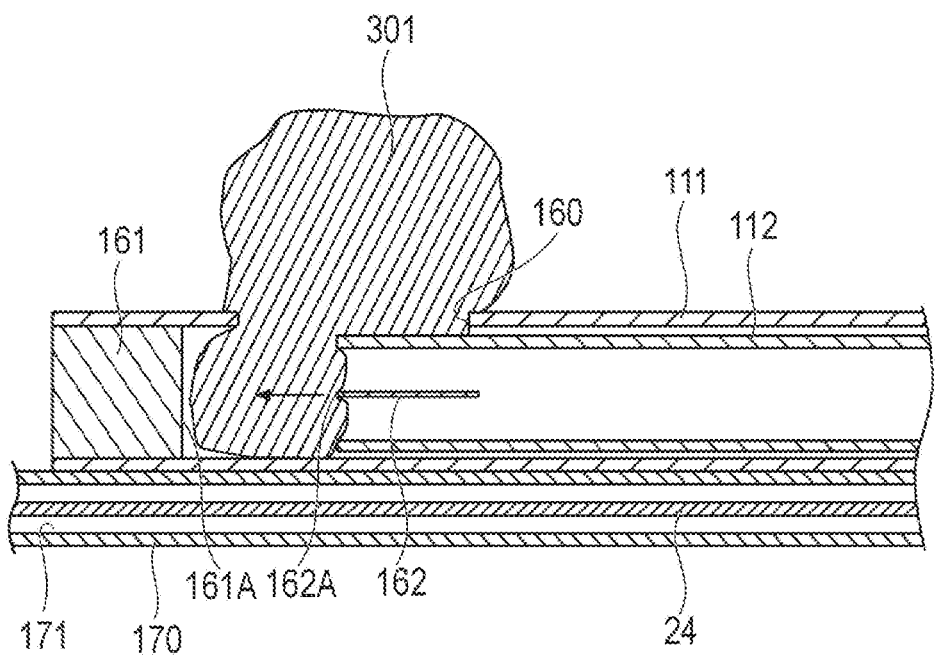
FIG. 20 is an enlarged sectional view illustrating the distal part of the removing device illustrating how the inner tube cuts out the thrombus which has been suctioned into the opening part of the outer tube.

After the plunger of the syringe 150 is pulled out, the shaft inner tube 112 is moved in the axial direction relative to the shaft outer tube 111. As the shaft inner tube 112 is moved toward the distal side of the shaft outer tube 111 or moved in such a way that the shaft inner tube 112 approaches the attachment part 161 from the proximal side with respect to the opening part 160, a portion of the thrombus 301 which has entered the hollow part inside of the shaft outer tube 111 from the opening part 160 is compressed and cut out by the distal face of the shaft inner tube 112, as illustrated in FIG. 20.

Figure 21:
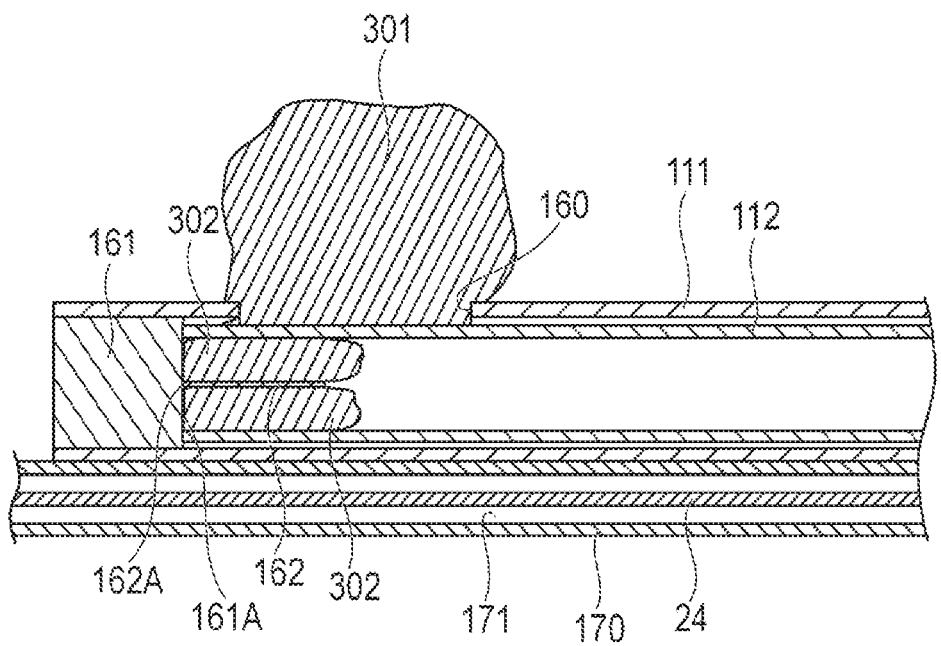
FIG. 21 is an enlarged sectional view illustrating the distal part of the removing device illustrating how the thrombus which has been cut out by the inner tube is cut by a cutting part.

The shaft inner tube 112 is moved to such an extent that the distal face of the shaft inner tube 112 comes into contact with the attachment face 161A of the attachment part 161 so that a cut off thrombus portion 302 settles down in the hollow part inside of the shaft inner tube 112, as illustrated in FIG. 21. At this time, the thrombus portion 302 is cut into two parts by the blade 162A of the cutting part 162 which is provided at the distal part of the shaft inner tube 112. As the shaft inner tube 112 comes into contact with the attachment face 161A of the attachment part 161, the blade 162A also comes into contact with the attachment face 161A. At this time, the thrombus portion 302, which has been cut off in the hollow part inside of the shaft outer tube 111, is cut by the blade 162A while it is pressed against the attachment part 161. Therefore, the blade 162A surely cuts the thrombus portion 302 which has been cut off, and the thrombus portion 302 is made into segments smaller than the inner diameter of the shaft inner tube 112. In this way, it is possible to prevent the cut off thrombus portion 302 from clogging the hollow part inside of the shaft inner tube 112.

Figure 22:
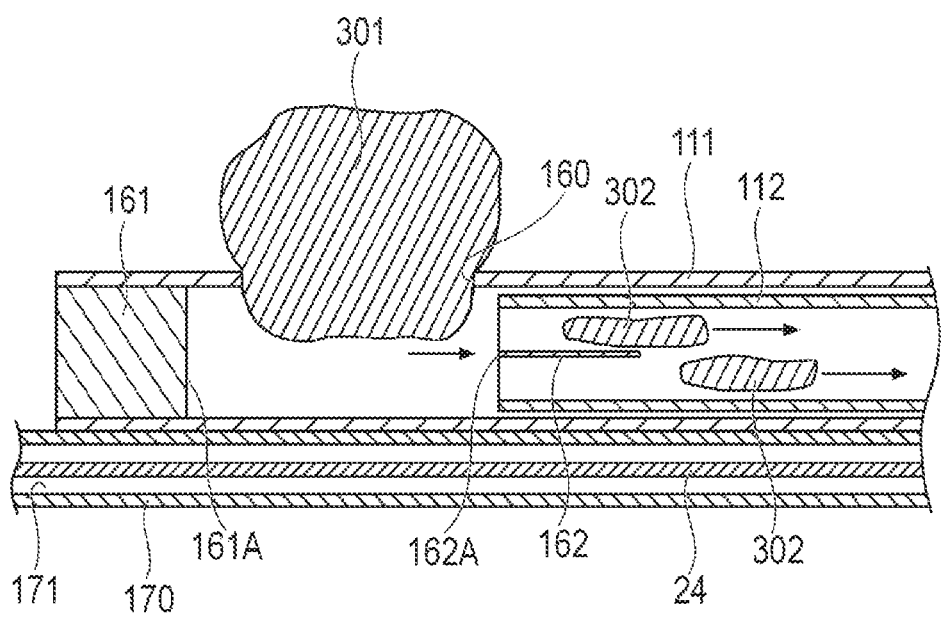
FIG. 22 is an enlarged sectional view illustrating the distal part of the removing device illustrating how the thrombus which has been cut by the cutting part is suctioned into the proximal side of the inner tube.

Since the hollow part of the shaft inner tube 112 remains evacuated by the syringe 150, the cut off thrombus portion 302 moves toward the proximal side of the hollow part of the shaft inner tube 112, as illustrated in FIG. 22. As the shaft inner tube 112 is moved toward the proximal side from the attachment part 161, the opening part 160 opens again and the thrombus portion 301 is suctioned into the hollow part of the shaft outer tube 111. Therefore, the thrombus portion 301 can be cut into small pieces and suctioned continuously by allowing the shaft inner tube 112 to reciprocate in the axial direction repeatedly.

Incidentally, while the thrombus portion 301 is being cut into small pieces, the opening part 160 remains closed, so that the suction of blood is suspended. This produces the effect of reducing the amount of blood to be suctioned.

It is desirable that the shaft outer tube 111 keeps rotating while the crushed thrombus portion 301 is being suctioned by the shaft main body 110. The continuously rotating shaft outer tube 111 produces an eddy current in the blood in the blood vessel. Thus, this allows the thrombus portions(s) 301 to gather together in the vicinity of the center (in the radial direction) of the blood vessel or the vicinity of the center around which the thrombus portion(s) 301 turn. This facilitates the suction of the thrombus portion(s) 301 from the opening part 160. In addition, the eddy current that has occurred in the vicinity of the opening part 160 also affects the flow in the hollow part of the shaft inner tube 112, thereby producing the eddy current also inside the shaft inner tube 112. The result is that resistance to flow in the axial direction decreases inside the shaft inner tube 112, thereby allowing the cut thrombus portion(s) 302 to be suctioned smoothly.

According to the exemplary embodiment, the shaft outer tube 111 keeps rotating and the shaft inner tube 112 keeps reciprocating in the axial direction relative to the shaft outer tube 111 while the thrombus portion(s) 301 is being suctioned. This action may be modified with additional actions, such as rotary action for the shaft inner tube 112 to turn differently from the shaft outer tube 111, (e.g., rotation in opposite direction or rotation at a different speed in the same direction). Such additional actions permit the thrombus portion(s) 301, which has been suctioned into the opening part 160, to be cut for certain and to be introduced into the hollow part of the shaft outer tube 111. Also, the additional reciprocating movement of the shaft outer tube 111 allows for crushing and stirring of the thrombus 300 in a broader region.

According to the exemplary embodiment, the blood flow is blocked by the medical device 10, so that the fragments of the crushed thrombus 300 float in the stagnant blood. This leads to the ability to efficiently suction the thrombus portion(s) 301 from the opening part 160 and remove thrombus portion(s) 301 from the blood vessel without allowing the thrombus portion(s) 301 to flow to another place. In the case where the blood is flowing, a strong suction force is required; however, this is not the case according to the exemplary embodiment, in which the blood flow is blocked and a suction force can be applied easily, so that the thrombus portion(s) 301 can be sucked more efficiently.

It is also possible to suck the thrombus 301 as illustrated in FIG. 23A. That is, the removing device 100 is pushed against the covering part 70 such that the proximal part of the covering part 70 is depressed, and the thrombus portion (s) 301 sticking to the covering part 70 is suctioned out of the opening part 160.

After the suction of the thrombus portion(s) 301 is complete, the reciprocal motion and rotary motion of the shaft outer tube 111 and the shaft inner tube 112 are suspended. The outermost sheath body 120 is moved in the axial direction, so that the stirring part 113 is housed, as illustrated in FIG. 23B. After that, the removing device 100 is pulled out from the blood vessel, with the expanding tool 20 remaining, as illustrated in FIG. 24A.

In the next step, the proximal side end part of the wire part 24 is inserted into the sheath 30 and the sheath 30 is inserted into the blood vessel along the expandable part 22, so that the sheath 30 approaches the vicinity of the wire part 24 and the covering part 70. Then, as illustrated in FIG. 24B, the sheath 30 is pushed in, with the proximal side end part of the wire part 24 held by hand so as to prevent its movement in the axial direction, and housed within the inside of the sheath 30, with the expandable part 22 and the covering part 70 contracted. It is to be noted that the expandable part 22 and the covering part 70 may be contracted before they are housed, with the pressing shaft 40 inserted into the inside of the sheath 30. When the covering part 70 is housed inside the sheath 30, the thrombus portion(s) 301 sticking to the covering part 70 is also housed in the sheath 30. Alternatively, it is possible to move the covering part 70 in contact with the inner wall of the blood vessel toward the proximal direction and scrape off the thrombus portion(s) 301 sticking to the blood vessel with the help of the covering part 70 and finally house the thrombus portion(s) 301 within the sheath 30 together with the covering part 70. By forming a gap between the distal side end part 74 of the covering part 70 and the expandable part 22, the gap reduces frictional resistance between the covering part 70 and the expandable part 22, thereby reducing resistance that occurs when the covering part 70 and the expandable part 22 are housed in the sheath 30, thus facilitating the housing thereof. Finally, the expanding tool 20 is pulled out of the blood vessel, together with the sheath 30. In this way, the treatment is completed.

As mentioned above, the medical device 10 according to the exemplary embodiment is designed to block the flow of fluid in the lumen of the living body when it is inserted into the lumen of the living body. The medical device 10 includes the long shaft part 23, the expandable part 22, and the covering part 70. The expandable part 22 is an elastically deformable cylindrical body with a plurality of pores 21A, which takes on a shape such that its central part becomes larger in outer diameter than both of its end parts while it is in its natural state, without external forces, and the cylindrical body has its proximal part connected to the shaft part 23. The covering part 70 takes on a cylindrical shape surrounding an outer periphery of the expandable part 22 and is flexible and deformable independently of the expandable part 22. The proximal part of the cylindrical shape is connected to a proximal part of the expandable part 22 or to the shaft member located at a proximal side with respect to the expandable part 22. The covering part 70 includes a space in the radial direction between the distal side end part of the cylindrical shape and the expandable part.

The medical device 10 constructed as mentioned above allows the expandable part 22 and the covering part 70 to be released from the sheath 30. The released expandable part 22 expands by its own elastic force in conformity with the shape of the lumen of the living body, so that the covering part 70 is pressed by the expandable part 22 against the lumen of the living body. Thus, the expandable part 22, which expands with its own elastic force, expands the inner diameter of the lumen of the living body to which the medical device is applied. In addition, the covering part 70 effectively blocks the flow in the lumen of the living body, allowing a substance (thrombus) to be effectively removed from the lumen of the living body. Moreover, a gap is formed between the distal side end part 74 of the covering part 70 and the expandable part 22, and this gap causes the covering part 70 to be pressed against the lumen of the living body only at the proximal side. This facilitates the positioning in the lumen of the living body and leads to improved operability. Moreover, the fact that a gap is formed between the distal side end part 74 of the covering part 70 and the expandable part 22 contributes to reduction of frictional resistance between the covering part 70 and the expandable part 22. This smoothens the sliding motion between the covering part 70 and the expandable part 70, which change in length differently in the axial direction at the time of expansion and contraction in the radial direction. The result is a reduction in the resistance which is encountered when the covering part 70 and the expandable part 22 are pushed out of the sheath 30 or housed in the sheath 30, and thus leads to improved operability.

In addition, the small-diameter part 22C of the expandable part 22 has an outer diameter which is smaller than the inner diameter of the covering part 70. This helps to form a gap between the small-diameter part 22C and the covering part 70.

In addition, the expandable part 22 is a cylindrical body formed by braiding from a plurality of wires 21 which are elastically deformable. The expandable part 22 has the small-diameter part 22C surrounded by the end part 74 of the distal side of the covering part 70 and the expandable part 22 also has the proximal side large-diameter part 22B and the distal side large-diameter part 22D which are capable of expanding in outer diameter more than the small-diameter part 22C and which hold between them the small-diameter part 22C in the axial direction. This structure permits the expandable part 22 to largely expand in outer diameter by its own elastic force and also permits the proximal side large-diameter part 22B to come into contact with the covering part 70, thereby forming a gap between the small-diameter part 22C and the covering part 70.

In addition, each one of the wires 21 takes on a shape (in the absence of external fore) such that the position constituting the proximal side large-diameter part 22B and distal side the large-diameter part 22D has the curvature radius r1 which is smaller than the curvature radius r2 of the position constituting the small-diameter part 22C. This permits the expandable part 22 to deform in such a way that the wires 21 bend more gently at the proximal side large-diameter part 22B and the distal side large-diameter part 22D than at the small-diameter part 22C. The result is that the proximal side large-diameter part 22B and the distal side large-diameter part 22D have the outer diameter which is larger than the outer diameter of the small-diameter part 22C.

When the expandable part 22 is surrounded by the covering part 70 and is in its natural state under the influence of its own elastic force, at least one of its proximal side or its distal side is depressed toward the inside thereof. This permits the expandable part 22 to greatly expand and also permits the outer diameter of the expandable part 22 to expand at that position where the end part of the proximal side of the expandable part 22 is depressed. This helps provide the gap between the end part 74 of the distal side of the covering part 70 and the expandable part 22. Moreover, this helps reduce or minimize the length in the axial direction of the expandable part 22 and the covering part 70 as much as possible, thereby allowing for compact placement at a desired position. This allows the stirring part 113 to keep a large cutting range and facilitates the visual observation with X-ray radioscopy, thereby leading to improved operability. Moreover, this also permits the depressed part to hold the thrombus portion(s) securely at the proximal side of the covering part 70. Incidentally, the depressed part may be formed at only one end side of the covering part 70.

In addition, the covering part 70 has a uniform outer diameter over a prescribed range in the axial direction at the end part 74 of the distal side, and the expandable part 22 has a position which decreases in outer diameter toward the distal side over the range surrounded by the covering part 70. This helps make the outer diameter uniform at the distal side of the covering part 70, thereby providing a gap between the end part 74 of the distal side of the covering part 70 and the expandable part 22.

In addition, the covering part 70 has its end part 74 at the proximal side positioned between the proximal side large-diameter part 22B of the expandable part 22 and the distal side large-diameter part 22D of the expandable part 22. This permits the inside of the covering part 70 to come into contact with the proximal side large-diameter part 22B, so that a gap is formed between the end part 74 of the distal side of the covering part 70 and the expandable part 22.

In addition, there is a gap between the end part 74 of the distal side of the covering part 70 and the small-diameter part 22C, which is positioned between the two large-diameter parts, one being the proximal side large-diameter part 22B and one being the distal side large-diameter part 22D. This gap becomes shorter as it comes close to the proximal side large-diameter part 22B. As a result, the covering part 70 keeps its inside in contact with the proximal side large-diameter part 22B while maintaining the gap between the end part 74 of the distal side of the covering part 70 and the small-diameter part 22C of the expandable part 22.

Further, the gap between the end part 74 of the distal side of the covering part 70 and the expandable part 22 becomes larger as the covering part 70 and the expandable part 22 are pushed out of the sheath 30 from the state of being housed in the sheath. As a result, the covering part 70 and the expandable part 22 can be compactly housed in the sheath 30 even though there is a gap between the covering part 70 and the expandable part 22.

In addition, the end part 74 of the distal side of the covering part 70 gets closer to the position of the distal side large-diameter part 22D of the expandable part 22 at the time of expansion than at the time of contraction. In other words, the length (in the axial direction) of the expandable part 22 becomes shorter at the time of expansion than at the time of contraction, so that the expandable part 22 can greatly expand in the radial direction.

The inner diameter of the end part 74 of the distal side of the covering part 70 is smaller than the outer diameter of the proximal side large-diameter part 22B when the expandable part 22 takes on its natural state. For this reason, the expandable part 22 is restrained from being completely expanded by the covering part 70, resulting in a high pressing force against the blood vessel.

In addition, the disclosure herein provides the method for treatment with the help of the above-mentioned medical device 10, the treatment being intended to remove by suction any object that has occurred in a lesion part in the lumen of the living body. The method includes gradually pushing out the expandable part 22 and the covering part 70 from the sheath 30 to the downstream side beyond the lesion part in the lumen of the living body, allowing the expandable part 22 to expand by its own elastic force, and causing the covering part 70 to come into contact with the lumen of the living body, while securing a gap between the end part 74 of the distal side of the covering part 70 and the expandable part 22; crushing or dissolving the object that has occurred in the lesion part in the lumen of the living body; inserting the device 100 provided with a suction mouth capable of suction into the lumen of the living body, thereby suctioning the crushed or dissolved object; causing the expandable part 22 and the covering part 70 to contract; and pulling the medical device 10 out of the lumen of the living body.

The method for treatment as described above offers the following advantages. The expandable part 22 and covering part 70 are released from the sheath 30, so that the expandable part 22 expands by its own elastic force in conformity with the shape of the lumen of the living body, thereby allowing the covering part 70 to be pushed against the lumen of the living body by the expandable part 22. Thus, the expandable part 22, which expands by its own elastic force, expands the inner diameter of the lumen of the living body to which the foregoing method is applied and the covering part 70 effectively blocks the flow of fluid in the lumen of the living body, thereby effectively allowing for the removal of the substance from the lumen of the living body. Moreover, because a gap is formed between the distal side end part 74 of the covering part 70 and the expandable part 22, the covering part 70 is pressed against the lumen of the living body within a limited position at the proximal side. This facilitates the positioning relative to the lumen of the living body. Moreover, because a gap is formed between the distal side end part 74 of the covering part 70 and the expandable part 22, the frictional resistance between the covering part 70 and the expandable part 22 decreases, thereby smoothening sliding motion between the covering part 70 and the expandable part 22. This leads to reduction in resistance encountered when the covering part 70 and the expandable part 22 are pushed out of the sheath 30 or housed into the sheath 30, and thus contributes to the improved operability.

The disclosure here is not restricted in its scope to the exemplary embodiment described above; it may be variously modified within its scope by those who are skilled in the art. For example, the exemplary embodiment is designed such that the medical device 10 is placed in the patient's body from an upstream side of the affected part. However, the position may be changed to downstream side of the affected part. In case of placement from the downstream side (the lung side) to the upstream side (the periphery side), the medical device 10 is moved to the affected part against the blood flow. After placement at the affected part, the expandable part 22 is expanded and the covering part 70 is also expanded. Thus, the blood flow is blocked and hence the blood vessel at the downstream side becomes smaller in inner diameter than the blood vessel at the upstream side. The result is that the opening part 160 gets near the blood vessel in inner diameter, which facilitates the suction of the thrombus from the affected part.

In addition, according to the exemplary embodiment, the removing device 100 provided with the stirring part 113 is used to crush the thrombus 300; however, the medical device 10 may be used to effectively dissolve the thrombus with the help of a thrombolytic agent rather than crush the thrombus 300. Blocking the blood flow by means of the medical device 10 permits the thrombolytic agent to stay around the thrombus, and this helps effectively dissolve the thrombus.

In addition, the medical device 10 to be inserted into the lumen of the living body is not only the blood vessel but also vasculum, urinary duct, bile duct, oviduct, hepatic duct, and so on. Moreover, the removing device is not restricted in configuration to that mentioned above.

Further, according to the above-mentioned embodiment, the expandable part 22 is constructed such that the end part in the axial direction is depressed toward the inside of the expandable part 22. This structure may be modified as illustrated in FIG. 25A, in which the end part in the axial direction of an expandable part 200 is not depressed. Moreover, a large-diameter part 201 may be provided at only one of the proximal side or distal side. Also, if the large-diameter part 201 is provided at only the proximal side, the expandable part 200 expands in such a way that the proximal part having a large outer diameter comes into strong contact with the lumen of the living body and the proximal part is fixed. This facilitates placement of the device in the lumen of the living body.

In addition, another modification as illustrated in FIG. 25B is also possible. According to this modification, an expandable part 210 has the central part 211, in the axial direction, which has a uniform outer diameter and the expandable part 210 is surrounded by a covering part 220 which fans out. That is, the outer diameter of the distal part of the covering part 220 increases in going toward the distal side. Even such a configuration can form a gap between the end part 221 of the distal side of the covering part 220 and the expandable part 210.

Figure 26:
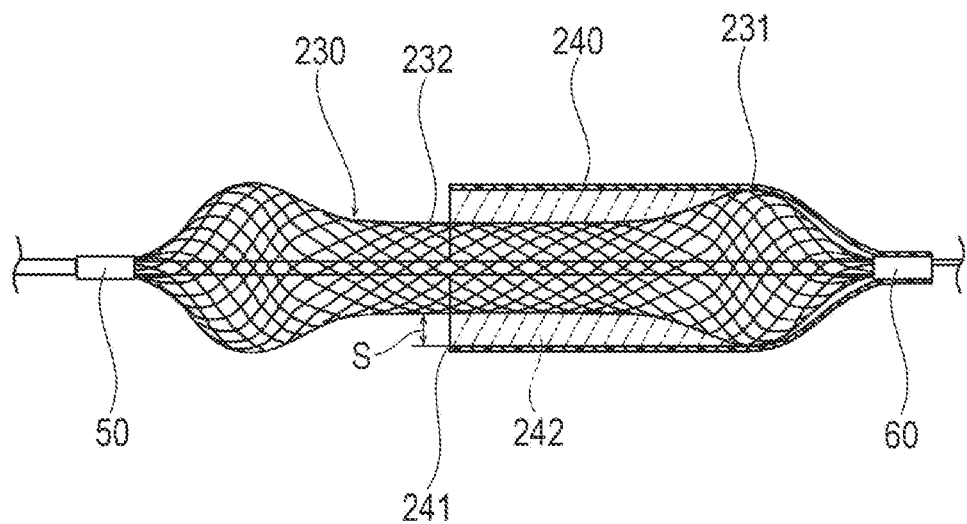
FIG. 26 is a plan view illustrating another modified example of the expandable part of the expanding tool and of the covering part.

Another modification as illustrated in FIG. 26 is also possible. According to this modification, an expandable part 230 and a covering part 240 are separated from each other with a cylindrical space 242 held between them, in an extent ranging from the position at which the covering part 240 comes into contact with a proximal side large-diameter part 231 to the end part 241 of the distal side of the covering part 240. The expandable part 230 takes on an expanded state (the third contracted state) in the covering part 240. The cylindrical space 242 between the expandable part 230 and the covering part 240 defines a length S (thickness) in the radial direction such that it increases or remains constant in going toward the distal side over the extent ranging from the position at which the proximal side large-diameter part 231 is in contact with the covering part 240 to the end part 241 of the distal side of the covering part 240. Therefore, the length S does not decrease in going to the distal side over the extent ranging from the position at which the proximal side large-diameter part 231 is in contact with the covering part 240 to the end part 241 of the distal side of the covering part 240. Consequently, when the expandable part 230 and the covering part 240 are pushed out of the sheath 30 or housed into the sheath 30, the portion of the distal side with respect to the proximal side large-diameter part 231 of the expandable part 230 hardly comes into contact with the covering part 240. Thus, the expandable part 230 and the covering part 240 can be easily pushed out of the sheath 30 or housed (retracted) into the sheath 30.

Figure 27:
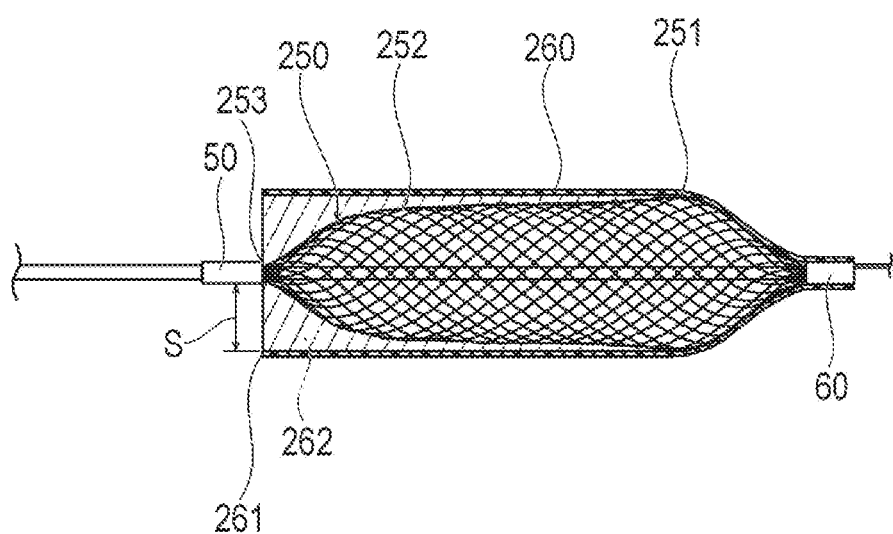
FIG. 27 is a plan view illustrating a further modified example of the expandable part of the expanding tool and of the covering part.

In addition, another modification as illustrated in FIG. 27 is also possible. According to this modification, an expandable part 250 and a covering part 260 are separated from each other with a cylindrical space 262 held between them, in an extent ranging from the position at which the covering part 260 comes into contact with a proximal side large-diameter part 251 to the end part 261 of the distal side of the covering part 260. The expandable part 250 takes on an expanded state (the third contracted state) in the covering part 260. The end part 261 of the distal side of the covering part 260 coincides with the end part 253 of the distal side of the expandable part 250. The cylindrical space 262 between the expandable part 250 and the covering part 260 defines a length S in the radial direction such that it increases in going toward the distal side over the extent ranging from the position at which the proximal side large-diameter part 251 is in contact with the covering part 260 to the end part 261 of the distal side of the covering part 260. Therefore, the length S does not decrease and does not remain constant in going to the distal side over the extent ranging from the position at which the proximal side large-diameter part 251 is in contact with the covering part 260 to the end part 261 of the distal side of the covering part 260. Consequently, when the expandable part 250 and the covering part 260 are pushed out of the sheath 30 or housed into the sheath 30, that portion of the distal side with respect to the proximal side large-diameter part 251 of the expandable part 250 hardly comes into contact with the covering part 260. Thus, the expandable part 250 and the covering part 260 can be easily pushed out of the sheath 30 or housed into the sheath 30.

A further modification as illustrated in FIG. 28 is also possible. According to this modification, an expandable part 270 and a covering part 280 are separated from each other with a cylindrical space 282 held between them, in an extent ranging from the position at which the covering part 280 comes into contact with a proximal side large-diameter part 271 to the end part 281 of the distal side of the covering part 280. The expandable part 270 takes on an expanded state (the third contracted state) in the covering part 280. The end part 281 of the distal side of the covering part 280 is at a position which is closer to the distal side than the end part 273 of the distal side of the expandable part 270. The cylindrical space 282 between the expandable part 270 and the covering part 280 has a length S in the radial direction such that it increases in going toward the distal side over the extent ranging from the position at which the proximal side large-diameter part 271 is in contact with the covering part 280 to the end part 273 of the distal side of the expandable part 270. Therefore, the length S does not decrease and does not remain constant in going to the distal side over the extent ranging from the position at which the proximal side large-diameter part 271 is in contact with the covering part 280 to the end part 281 of the distal side of the covering part 280. Consequently, when the expandable part 270 and the covering part 280 are pushed out of the sheath 30 or housed into the sheath 30, that portion of the distal side with respect to the proximal side large-diameter part 271 of the expandable part 270 hardly comes into contact with the covering part 280. Also, since the end part 273 of the distal side of the expandable part 270 is positioned inside the covering part 280, the expandable part 270 and the covering part 280 hardly come into contact with each other. Thus, the expandable part 270 and the covering part 280 can be easily pushed out of the sheath 30 or housed into the sheath 30.

In addition, another modification illustrated in FIG. 29 is also possible. According to this modification, an expandable part 290 and a covering part 310 are separated from each other with a cylindrical space 312 held between them, in an extent ranging from the position at which the covering part 310 comes into contact with a proximal side large-diameter part 291 to the end part 311 of the distal side of the covering part 310. The expandable part 290 takes on an expanded state (the third contracted state) in the covering part 310. The end part 311 of the distal side of the covering part 310 coincides with the end part 293 of the distal side of the expandable part 290. There exists inside the covering part 310 a small-diameter part 292 whose outer diameter is smaller than the inner diameter of the covering part 310 and a distal side large-diameter part 294. With this configuration, the portion of the distal side with respect to the proximal side large-diameter part 291 of the expandable part 290 hardly comes into contact with the covering part 310. This permits the expandable part 290 and the covering part 310 to be easily pushed out of the sheath 30 and housed into the sheath 30.

In addition, the distal side connecting part 50, the proximal side connecting part 60 and the wires 21 may be made at least partly from a material containing an X-ray radiopacity material. For example, a portion of the plurality of wires 21 may be made of a material containing an X-ray radiopacity material. The resulting wires help confirm the position of the device during X-ray radiopacity, which facilitates manipulation. Among preferable X-ray radiopacity material are, for example, gold, platinum, platinum-iridium alloy, silver, stainless steel, molybdenum, tungsten, tantalum, palladium, and alloys thereof.

The detailed description above describes a medical device and a method for treatment. The invention is not limited, however, to the precise embodiments and variations described. Various changes, modifications and equivalents could be effected therein by one skilled in the art without departing from the spirit or scope of the disclosure as defined by the appended claims. It is expressly intended that all such changes, modifications and equivalents which fall within the scope of the claims are embraced by the claims.

What is claimed is:

1. A medical device configured to be inserted into a lumen of a living body so as to block a flow in the lumen of the living body, the medical device comprising:
    an elongated shaft part;
    an expandable part; and
    a covering part,
    the expandable part being an elastically deformable cylindrical body with a plurality of pores, the cylindrical body having a first end and a second end, and a proximal part connected to the elongated shaft part, and
    the covering part being flexible and deformable independent of the expandable part, the covering part having a cover proximal part connected to the proximal part of the expandable part or connected to the elongated shaft part located at a proximal side with respect to the expandable part,
    wherein the expandable part is configured to obtain an expanded shape in which a central part of the cylindrical body has a larger outer diameter than an outer diameter of both the first end and the second end of the cylindrical body, when the expandable part is in a natural state in the absence of external forces,
    wherein the covering part is configured to have a cylindrical shape surrounding an outer periphery of the expandable part such that a space is defined in a radial direction between a distal side end part of the cylindrical shape and the expandable part, and
    wherein the cylindrical body of the expandable part is braided from a plurality of elastically deformable wires and includes a small-diameter part and at least one large-diameter part, the small-diameter part being surrounded by an end part of a distal side of the covering part, and the at least one large-diameter part being configured to expand to a larger outer diameter than an outer diameter of the small-diameter part.

2. The medical device as defined in claim 1, wherein the covering part has a uniform outer diameter over a prescribed range in an axial direction at an end part of a distal side, and the expandable part includes a portion which decreases in outer diameter toward the distal side over an extent surrounded by the covering part.

3. The medical device as defined in claim 1, wherein the expandable part and the covering part form between them a space in the radial direction whose length increases or remains constant toward the distal side over an extent ranging from a position at which the at least one large-diameter part located at a proximal side of the small-diameter part is in contact with the covering part to the end part of the distal side of the covering part.

4. The medical device as defined in claim 1, further comprising a sheath capable of housing the expandable part and the covering part in a contracted state, a length in the radial direction of the space between the end part of the distal side of the covering part and the expandable part increasing as the covering part and expandable part, which have been housed in the sheath, are pushed out of the sheath.

5. The medical device as defined in claim 1, wherein the at least one large-diameter part includes a first large-diameter part and a second large-diameter part, the first large-diameter part and the second large-diameter part being located at a distal side and a proximal side, respectively, relative to the small-diameter part.

6. The medical device as defined in claim 5, wherein the end part of the distal side of the covering part is located between the first and second large-diameter parts of the expandable part.

7. The medical device as defined in claim 1, wherein the at least one large-diameter part is located at a proximal side relative to the small-diameter part.

8. The medical device as defined in claim 1, wherein the expandable part has a maximum outer diameter larger than a maximum inner diameter of the covering part, when the expandable part is not covered by the covering part and when the expandable part is in a natural state in the absence of external forces.

9. The medical device as defined in claim 1, wherein the plurality of elastically deformable wires include at least a first wire and a second wire, the first wire and the second wire being different in outer diameter.

10. The medical device as defined in claim 1, wherein the covering part includes a cover distal part, the cover distal part not being connected to the expandable part or the elongated shaft part such that the covering part is only fastened at the cover proximal part and the covering part is thus configured to deform independently from the expandable part.

11. A method for treatment to remove by suction an obstruction that has occurred in a lesion part in a lumen of a living body, the method comprising:
providing a medical device comprising an elongated shaft part, an expandable part, a covering part, and a sheath configured to house the expandable part and the covering part in a contracted state, the expandable part being an elastically deformable cylindrical body with a plurality of pores, the cylindrical body having a first end and a second end, and a proximal part connected to the elongated shaft part; and the covering part being flexible and deformable independent of the expandable part, the covering part having a cover proximal part connected to the proximal part of the expandable part or connected to the elongated shaft part located at a proximal side with respect to the expandable part, and the expandable part having a maximum outer diameter larger than a maximum inner diameter of the covering part, when the expandable part is not covered by the covering part and when the expandable part is in a natural state in the absence of external forces, and wherein in the expanded state, the covering part has a uniform outer diameter over a predefined range in an axial direction at a distal side end part, and the expandable part includes a portion which decreases in outer diameter toward the distal side over an extent surrounded by the covering part, whereby a gap is formed between the distal side end part of the expandable part and the expandable part;
pushing the expandable part and the covering part out from the sheath to a downstream side beyond the lesion part in the lumen of the living body;
allowing the expandable part to expand by its own elastic force, and causing the covering part to come into contact with the lumen of the living body, while securing a space between the end part of the distal side of the covering part and the expandable part;
crushing or dissolving an obstruction that has occurred in the lesion part in the lumen of the living body;
inserting a device provided with suction into the lumen of the living body, thereby suctioning the crushed or dissolved obstruction; and
housing the expandable part and covering part in the sheath in a contracted state; and
pulling the medical device out of the lumen of the living body.

12. The method for treatment as defined in claim 11, further comprising:
blocking a flow of fluid in the lumen of the living body when the covering part is in contact with the lumen of the living body.

13. The method for treatment as defined in claim 11, further comprising:
forming the gap between a distal side end part of the covering part and the expandable part.

14. A medical device comprising:
an expandable part configured for elastic deformation, the expandable part having an expanded state when in a natural state in the absence of external forces;
a covering part including a flexible and deformable tubular member surrounding an outer periphery of the expandable part; and
a shaft part extending through the expandable part and the covering part;
wherein the covering part is only fastened to the expandable part at a cover proximal part such that the covering part is configured for deformation independently from the expandable part;
wherein the expandable part has a maximum outer diameter larger than a maximum inner diameter of the covering part, when the expandable part is not covered by the covering part and when the expandable part is in a natural state in the absence of external forces; and
wherein, in the expanded state, the covering part has a uniform outer diameter over a predefined range in an axial direction at a distal side end part, and the expandable part includes a portion which decreases in outer diameter toward the distal side over an extent surrounded by the covering part, whereby a gap is formed between the distal side end part of the expandable part and the expandable part.

15. The medical device as defined in claim 14, wherein the covering part includes folds in an axial direction when in a contracted state.

16. The medical device as defined in claim 14, wherein the expandable part comprises a plurality of intertwined elastically deformable wires.

17. The medical device as defined in claim 16, wherein the plurality of elastically deformable wires include at least a first wire and a second wire, the first wire and the second wire being different in outer diameter.

18. The medical device as defined in claim 14, further comprising a sheath, the sheath housing the expandable part and the covering part in a contracted state.

19. A medical device configured to be inserted into a lumen of a living body so as to block a flow in the lumen of the living body, the medical device comprising:
- an elongated shaft part;
- an expandable part; and
- a covering part,
- the expandable part being an elastically deformable cylindrical body with a plurality of pores, the cylindrical body having a first end and a second end, and a proximal part connected to the elongated shaft part, and
- the covering part being flexible and deformable independent of the expandable part, the covering part having a cover proximal part connected to the proximal part of the expandable part or connected to the elongated shaft part located at a proximal side with respect to the expandable part, wherein the expandable part is configured to obtain an expanded shape in which a central part of the cylindrical body has a larger outer diameter than an outer diameter of both the first end and the second end of the cylindrical body, when the expandable part is in a natural state in the absence of external forces, wherein the covering part is configured to have a cylindrical shape surrounding an outer periphery of the expandable part such that a space is defined in a radial direction between a distal side end part of the cylindrical shape and the expandable part, and wherein the expandable part has a maximum outer diameter larger than a maximum inner diameter of the covering part, when the expandable part is not covered by the covering part and when the expandable part is in a natural state in the absence of external forces.

* * * * *